(12) United States Patent
Politi et al.

(10) Patent No.: US 8,052,999 B2
(45) Date of Patent: Nov. 8, 2011

(54) GRANULES, TABLETS AND GRANULATION

(75) Inventors: Giovanni Politi, Helsinki (FI); Erkki Heilakka, Helsinki (FI)

(73) Assignee: Atacama Labs, Espoo (FI)

( * ) Notice: Subject to any disclaimer, the term of this patent is extended or adjusted under 35 U.S.C. 154(b) by 973 days.

(21) Appl. No.: 11/979,530

(22) Filed: Nov. 5, 2007

(65) Prior Publication Data

US 2008/0111269 A1 May 15, 2008

(30) Foreign Application Priority Data

| Nov. 10, 2006 | (FI) | .................................. | 20060990 |
| Dec. 21, 2006 | (FI) | .................................. | 20061146 |
| Jul. 2, 2007 | (FI) | .................................. | 20070521 |

(51) Int. Cl.
*A61K 9/14* (2006.01)
*A61K 9/22* (2006.01)

(52) U.S. Cl. ........................ 424/489; 424/464

(58) Field of Classification Search ........................ None
See application file for complete search history.

(56) References Cited

U.S. PATENT DOCUMENTS

| 3,923,974 | A | 12/1975 | Andrews |
| 4,161,516 | A | 7/1979 | Bell |
| 4,998,675 | A | 3/1991 | Mohrman |
| 5,137,732 | A | 8/1992 | Buehler et al. |
| 6,276,917 | B1 | 8/2001 | Gutierrez et al. |
| 6,752,939 | B2 | 6/2004 | Gereg |
| 2002/0034540 | A1 | 3/2002 | Price |
| 2003/0004182 | A1 | 1/2003 | Gierer |
| 2003/0068367 | A1 | 4/2003 | Sowden |
| 2003/0187167 | A1 | 10/2003 | Adams et al. |
| 2003/0228357 | A1 | 12/2003 | Johnson et al. |
| 2004/0126429 | A1 | 7/2004 | Storm et al. |
| 2008/0111269 | A1 | 5/2008 | Politi et al. |

FOREIGN PATENT DOCUMENTS

| DE | 44 18 029 | A1 | 11/1995 |
| GB | 1333646 | A | 10/1973 |
| GB | 1558153 | | 12/1979 |
| GB | 1558153 | A | 12/1979 |
| GB | 1 567 204 | | 5/1980 |
| JP | 52119474 | A | 10/1977 |
| JP | 4176372 | A | 6/1992 |
| JP | 06297197 | A | 10/1994 |
| JP | 1099672 | A | 4/1998 |
| WO | WO 92/19227 | A2 | 11/1992 |
| WO | WO 9219227 | A2 * | 11/1992 |

(Continued)

OTHER PUBLICATIONS

Maki, et al., "Modifying Drug Release and Tablet Properties of Starch Acetate Tablets by Dry Powder Agglomeration", Journal of Pharmaceutical Sciences, vol. 96, No. 2, Feb. 2007, pp. 438-447.

(Continued)

*Primary Examiner* — Susan Tran
(74) *Attorney, Agent, or Firm* — Birch, Stewart, Kolasch & Birch, LLP

(57) ABSTRACT

The invention provides, inter alia, a method for producing granules from a powder, characterized in that a low compaction force is applied to the powder to produce a compacted mass comprising a mixture of fine particles and granules and separating fine particles from the granules by entraining the fine particles in a gas stream. Also provided are apparatus for use in the process and tablets formed by compression of the resultant granules.

24 Claims, 20 Drawing Sheets

FOREIGN PATENT DOCUMENTS

| WO | WO 98/35672 A1 | 8/1998 |
| --- | --- | --- |
| WO | WO 99/11261 | 3/1999 |
| WO | WO-99/11261 A1 | 3/1999 |
| WO | WO 9911261 A1 * | 3/1999 |
| WO | WO 99/25343 A1 | 5/1999 |
| WO | WO 03/086343 A2 | 10/2003 |
| WO | 2004/108693 A | 12/2004 |
| WO | WO-2005/103137 A2 | 11/2005 |
| WO | WO 2006/048699 A1 | 5/2006 |
| WO | WO 2007/022113 A2 | 2/2007 |
| WO | WO 2007022113 A2 * | 2/2007 |
| WO | WO 2007/096906 A2 | 8/2007 |
| WO | WO 2008/056021 A2 | 5/2008 |
| WO | WO-2009/135946 A1 | 11/2009 |

OTHER PUBLICATIONS

Li, et al., "Interparticle van der Waals Force in Powder Flowability and Compactibility", International Journal of Pharmaceutics, vol. 280, 2004, pp. 77-93.

Rowley, "Quantifying Electrostatic Interactions in Pharmaceutical Solid Systems", International Journal of Pharmaceutics, vol. 227, 2001, pp. 47-55.

PCT/FI2007/000265 International Search Report, Form PCT/ISA/210, Mar. 26, 2009.

Search report from Finnish Patent Office, Application No. 20070521.

Peter Kleinebudde "Roll Compaction/Dry Granulation: Pharmaceutical Applications", European Journal of Pharmaceutics and Biopharmaceutics 58 (2004), pp. 317-326, *Institute of Pharmaceutics, Heinrich-Heine-University Duesseldorf*, Duesseldorf, Germany.

I. Inculet et al., "Generation of Bipolar Electric Fields During Industrial Handling of Powders", Chemical Engineering Science 61 (2006), pp. 2249-2253, *Dept. of Electrical and Computer Engineering, University of Western Ontario*, London, Ontario, Canada.

Scott Baker and Tim Herrman, "Evaluating Particle Size", Kansas State University, May 2002, *Deptpartment of Grain Science and Industry, Kansas State University Agricultural Experiment Station and Cooperative Extension Service*, Kansas, USA.

K.A. Rietma et al., "A Coherent Matrix Model for the Consolidation and Compaction of an Excipient With Magnesium Stearate", International Journal of Pharmaceutics, 97 (1993), pp. 195-203, *Department of Pharmaceutical Technology and Biopharmacy, University of Groningen* (The Netherlands) *and Organon International B.V., Oss* (The Netherlands), *1993 Elsevier Science Publishers B.V.*

International Search Report for Application PCT/EP2009/055627, dated Jul. 7, 2010.

* cited by examiner

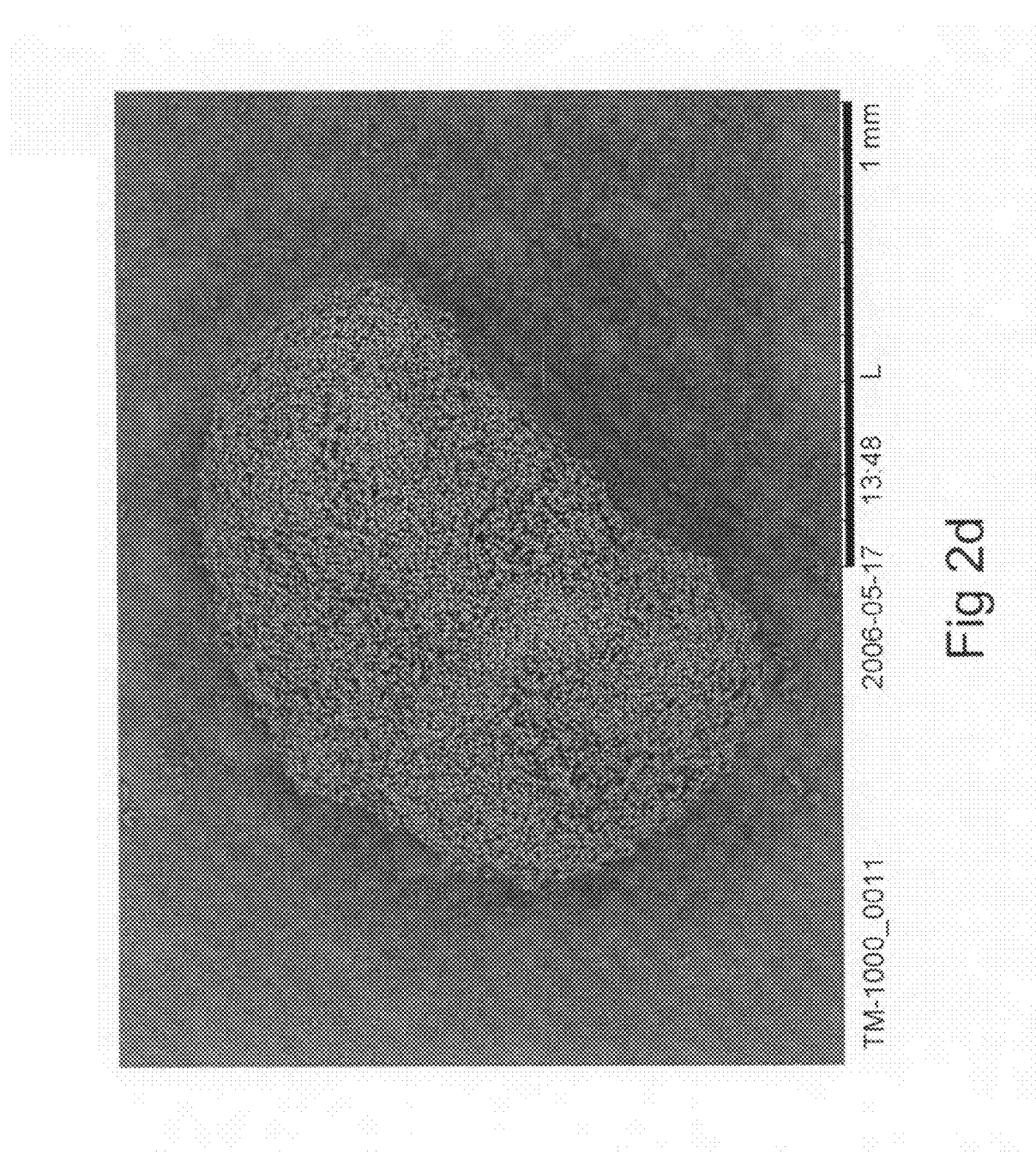

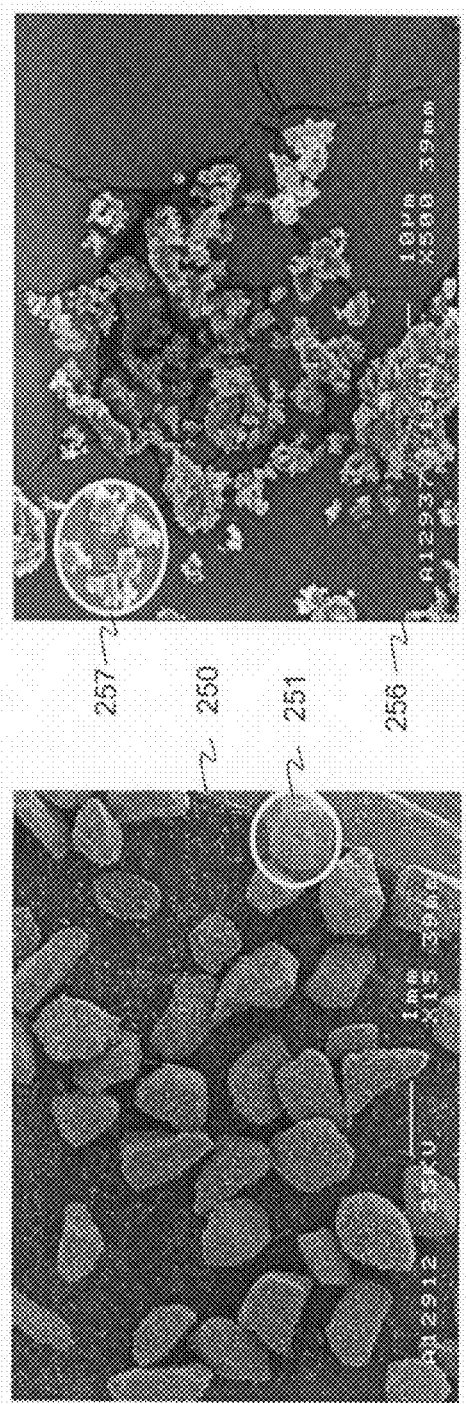
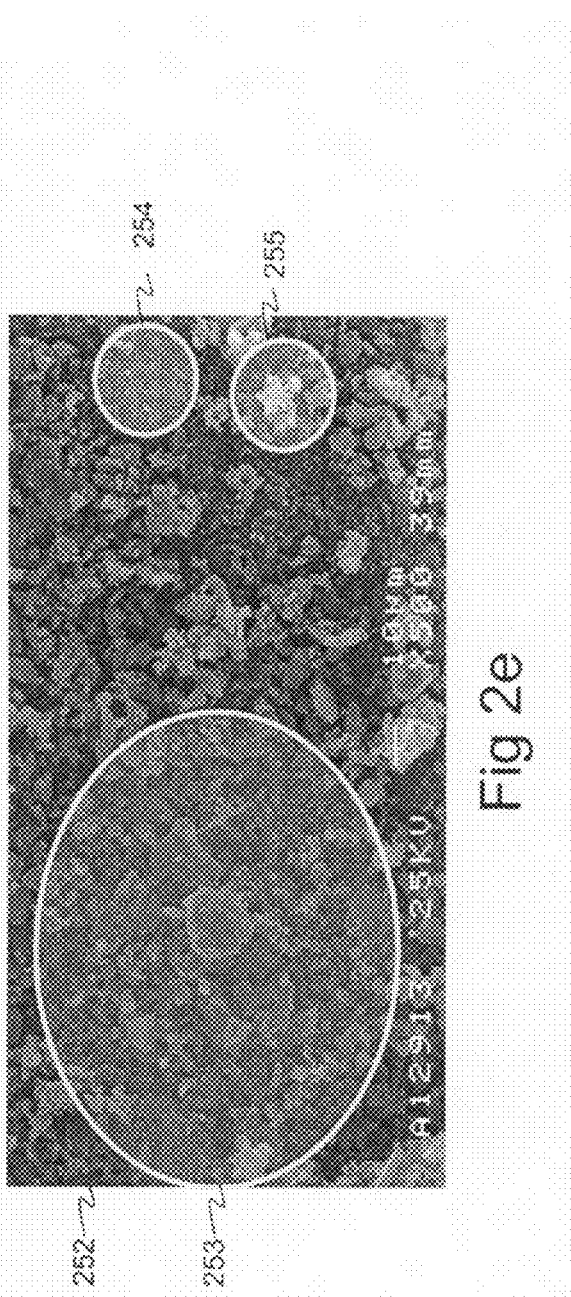
Fig 2e

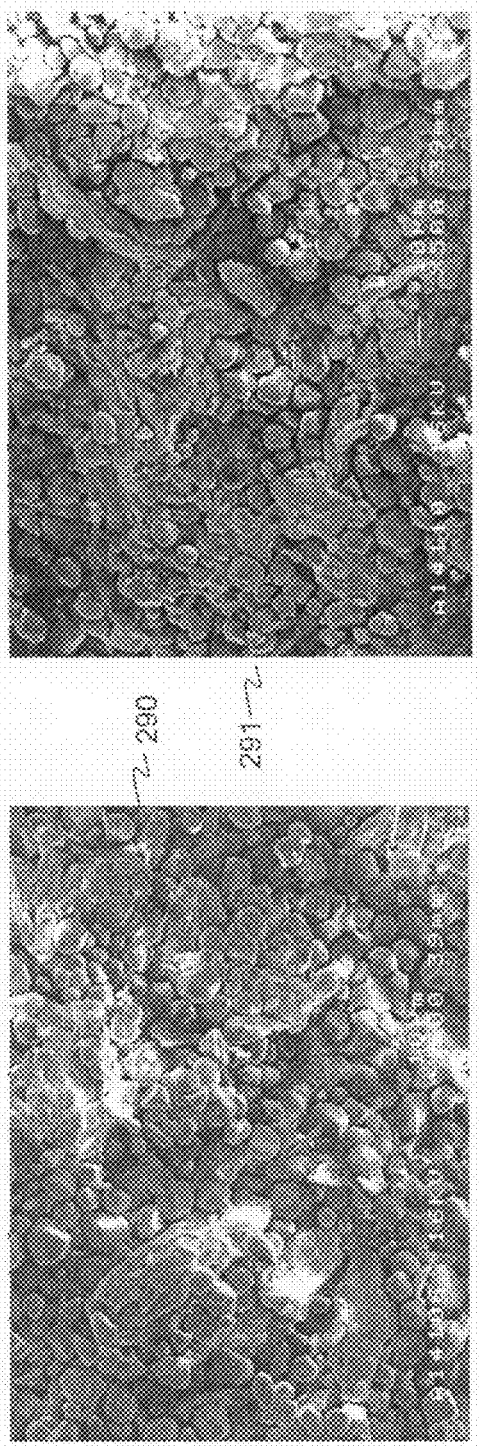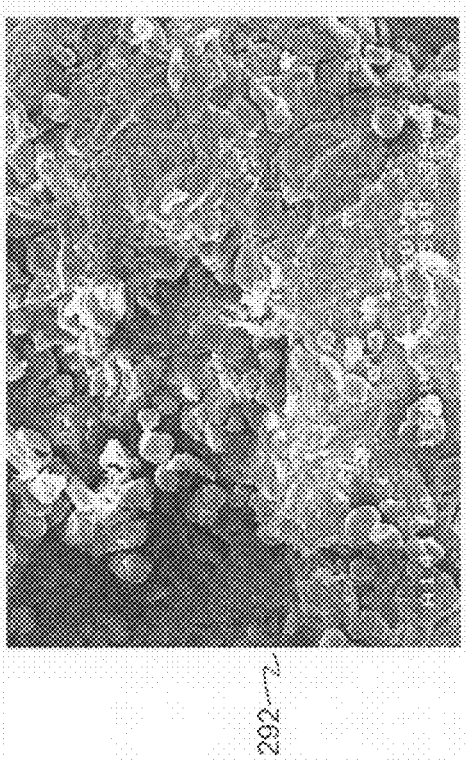
Fig 2i

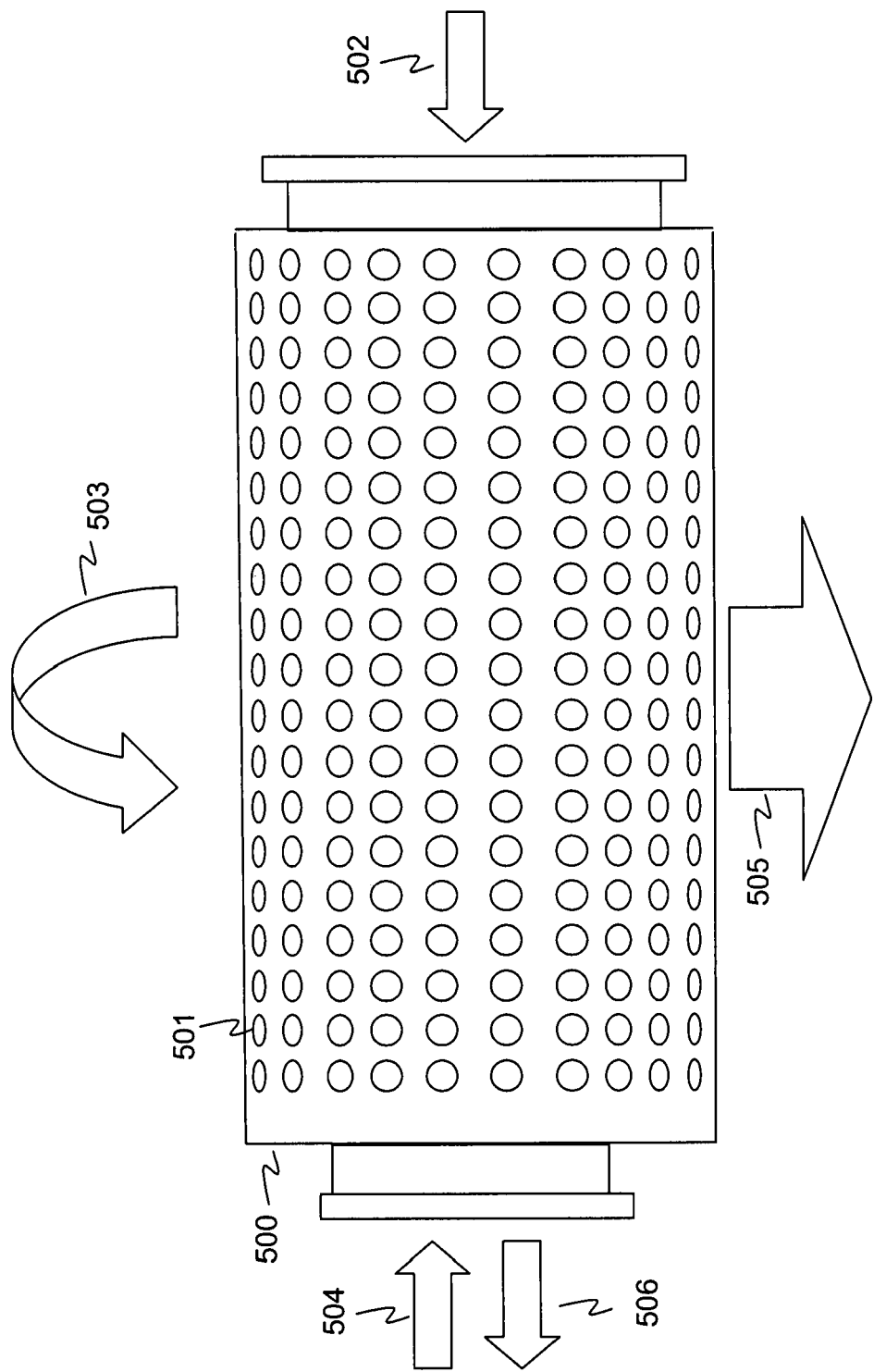

GRANULES, TABLETS AND GRANULATION

TECHNICAL FIELD OF INVENTION

The invention relates to granules and tablets and method and apparatus for their production.

The above-referenced patent application claims priority benefit from the foreign patent applications listed below:

Finland Application No. 20060990, filed Nov. 10, 2006;
Finland Application No. 20061146, filed Dec. 21, 2006; and
Finland Application No. 20070521, filed Jul. 2, 2007.

BACKGROUND OF THE INVENTION

Tablets are one of the most frequently employed delivery forms for most medicinal preparations. This situation can be explained by the fact that this dosage form allows for accurate dosage of the active component of the medicinal formulation. Furthermore, handling and packaging are easier and shelf life and stability of these preparations are generally better than those of other formulations.

These same arguments also explain the reason why tablets are often used as media for other applications such as food, including confectionery products, aromas or sweeteners, detergents, dyes or phytosanitary products.

A solid bulk of granulate mass, which is necessary for manufacturing tablets, can be manufactured using two main processes, wet granulation or dry granulation. Tablets may also be manufactured using direct compression. Direct compression relates to the tableting process itself rather than preparation of the starting material.

In wet granulation, components are typically mixed and granulated using a wet binder. The wet granulates are then sieved, dried and optionally ground prior to compressing into tablets. Wet granulation is used extensively in the pharmaceutical industry although it has proven to be a difficult method, mainly because the liquids needed in the granule and tablet manufacturing process often have an adverse effect on the characteristics of the active pharmaceutical ingredients (APIs) and/or on the end product such as a tablet.

Dry granulation is usually described as a method of controlled crushing of precompacted powders densified by either slugging or passing the material between two counter-rotating rolls. More specifically, powdered components that may contain very fine particles are typically mixed prior to being compacted to yield hard slugs which are then ground and sieved before the addition of other ingredients and final compression to form tablets. Because substantially no liquids are used in the dry granulation process, the issues related to wet granulation are avoided. Although dry granulation would in many cases appear to be the best way to produce products such as tablets containing APIs, it has been relatively little used because of the challenges in producing the desired kind of granules as well as managing the granulated material in the manufacturing process. Known dry granulation methods, as well as the known issues related to them are well described in scientific articles, such as the review article "Roll compaction/dry granulation: pharmaceutical applications" written by Peter Kleinebudde and published in European Journal of Pharmaceutics and Biopharmaceutics 58 (2004) at pages 317-326.

Direct compression is generally considered to be the simplest and the most economical process for producing tablets. However, it may only be applied to materials that don't need to be granulated before tableting. Direct compression requires only two principal steps; i.e., the mixing of all the ingredients and the compression of this mixture. However, direct compression is applicable to only a relatively small number of substances as the ingredients of the tablets often need to be processed by some granulation technique to make them compressible and/or for improving their homogeneity and flow-ability.

A component of a tablet is usually described as being either an excipient or an active ingredient. Active ingredients are normally those that trigger a pharmaceutical, chemical or nutritive effect and they are present in the tablet only in the amount necessary to provide the desired effect. Excipients are inert ingredients that are included to facilitate the preparation of the dosage forms or to adapt the release characteristics of the active ingredients, or for other purposes ancillary to those of the active ingredients.

Excipients can be characterized according to their function in the formulation as, for instance, lubricants, glidants, fillers (or diluents), disintegrants, binders, flavors, sweeteners and dyes.

Lubricants are intended to improve the ejection of the compressed tablet from the die of the tablet-making equipment and to prevent sticking in the punches.

Glidants are added to improve the powder flow. They are typically used to help the component mixture to fill the die evenly and uniformly prior to compression.

Fillers are inert ingredients sometimes used as bulking agents in order to decrease the concentration of the active ingredient in the final formulation. Binders in many cases also function as fillers.

Disintegrants may be added to formulations in order to help the tablets disintegrate when they are placed in a liquid environment and so release the active ingredient. The disintegration properties usually are based upon the ability of the disintegrant to swell in the presence of a liquid, such as water or gastric juice. This swelling disrupts the continuity of the tablet structure and thus allows the different components to enter into solution or into suspension Binders are used to hold together the structure of the tablets. They have the ability to bind together the other ingredients after sufficient compression forces have been applied and they contribute to the integrity of the tablets.

Finding the proper excipients for particular APIs and determining the proper manufacturing process for the combination of excipients and APIs can be a time-consuming job that may lengthen the design process of a pharmaceutical product, such as a tablet significantly, even by years.

Both the dry and wet granulation methods of the prior art may produce solid bridges between particles within granules that may be undesirable for example in that they lead to unsatisfactory subsequent tablet characteristics. The solid bridges may be caused by partial melting, hardening binders or crystallization of dissolved substances. Partial melting may for example occur when high compaction force is used in dry granulation methods. When the pressure in the compaction process is released, crystallization of particles may take place and bind the particles together. Introduction of hardening binders is common in pharmaceutical wet granulations when a binder is included in the granulating solvent. The solvent forms liquid bridges, and the binder will harden or crystallize on drying to form solid bridges between the particles. Examples of binders which can function in this way are polyvinylpyrrolidone, cellulose derivatives (e.g. carboxymethylcellulose) and pregelatinized starch. Substances, e.g. lactose, which can dissolve during a wet granulation process may subsequently crystallize on drying acting as a hardening binder.

Electrostatic forces may also be important in causing powder cohesion and the initial formation of agglomerates, e.g. during mixing. In general they do not contribute significantly to the final strength of the granule. Van der Waals forces, however, may be about four orders of magnitude greater than electrostatic forces and can contribute significantly to the strength of granules, e.g. those produced by dry granulation. The magnitude of these forces increases as the distance between particle surfaces decreases.

In addition to finding a practical manufacturing process for a pharmaceutical product, validation of the manufacturing process is essential. Validation means that the process must be able to reliably produce a consistently acceptable and predictable outcome each time the process is used. Wet granulation methods are quite challenging to manage in this respect. The wet granulation process is often quite vulnerable to small changes in manufacturing conditions. For example, variations in the moisture content of starch in the manufacturing process after drying may produce a tablet that is too hygroscopic or which has a reduced shelf life. When a pharmaceutical product is being developed in laboratory conditions, the conditions can be controlled relatively easily. However, the conditions available in mass production environments are typically less accurately controllable thus making validation of the manufacturing process a difficult and time consuming task. The same can be said about direct compression methods where the quality of the final product depends on the physical properties of the API and excipients. A small change in such properties can result, for example in segregation and flow-ability problems.

Because of the manufacturing and process validation issues related to wet granulation and direct compression methods, it is desirable, particularly in the pharmaceutical industry, to use dry granulation techniques whenever possible. However, the dry granulation methods known in the prior art produce granules that are seldom usable in a tablet manufacturing process. Conflicting process design parameters often lead to compromises where some qualities of the resulting granule product may be good, but other desirable qualities are lacking or absent. For example, the flow characteristics of the granules may be insufficient, the non-homogeneity of the granules may cause segregation in the manufacturing process or capping in tablets, or some of the granules may exhibit excessive hardness, all of which can make the tableting process very difficult, slow and sometimes impossible. Furthermore, the bulk granules may be difficult to compress into tablets. Alternatively or additionally, the disintegration characteristics of the resulting tablets may be sub-optimal. Such problems commonly relate to the non-homogeneity and granule structure of the granulate mass produced by the compactor. For instance, the mass may have too high a percentage of fine particles or some granules produced by the compactor may be too dense for effective tableting.

It is also well known in the art that in order to get uniform tablets the bulk to be tableted should be homogeneous and should have good flow characteristics.

In prior art dry granulation processes such as roll compaction, the resulting bulk is not generally homogeneously flowing, for example because of the presence of relatively large (1-3 mm) and dense granules together with very small (e.g. 1-30 micrometers) particles. This can cause segregation as the large, typically dense and/or hard granules of the prior art flow in a different way to the fine particles when the granulate mass is conveyed in the manufacturing process, e.g. during tableting. Because of the segregation, it is often difficult to ensure production of acceptable tablets. For this reason, in the art there are some known devices in which the small particles and sometimes also the biggest particles are separated from the rest of the granules with the help of a fractionating device such as (a set of) vibrating screen(s). This process is generally complicated and noisy and the result is a relatively homogeneously flowing bulk where the granules are hard and difficult to compress into tablets. Furthermore, the process of separating small particles from granules becomes very difficult if the material is sticky and the screen-size is not big enough. Generally in this process the apertures of the screen must have a minimum dimension of at least 500 μm.

Another problem which occurs in dry granulation methods of the prior art is the difficulty of preparing, in the development stage, a pilot bulk which is representative of the production bulk. Thus, the compaction forces and the other compaction parameters used at the laboratory scale can be very different from those used at the production scale. As a result the properties, e.g. flow-ability of the production bulk can be very different from that which has been prepared in a pilot facility. One sieving method applicable in laboratory scale is air sieving. One conventional air sieve involves passing a powder through a mesh of defined size in order to exclude particles below the specified size (the desired granules are retained above the mesh and the rejected particles pass below). Air is passed through the mesh to carry away the fine particles. The problem with the air sieves of the prior art is that their capacity is not sufficient for industrial production of granulate mass. Furthermore, the air sieves that rely on mesh size in the separation of rejected material often exclude desirable small granules from the acceptable granulate mass when separating out the fine particles from the mass. Yet further, fragile granules may break in the sieving process where undersize particles are sucked through the apertures of the sieve.

Patent application WO 99/11261 discloses dry-granulated granules that may comprise API only. In the method disclosed in the application, an air sieve known in the prior art is used for separating fine particles (particles and granules smaller than 150 or 125 micrometers) from granules comprising up to 100% of API. The sieving utilizes a sieve whose mesh size is about the maximum size of rejectable particles, e.g. 150 micrometers. It seems that the granules of the disclosure have been created using relatively high compaction forces since the proportion of fine particles (smaller than 125 micrometers) after compaction is at most around 26 percent (see table 1). The method results, following sieving, in a flowing homogeneous granulate mass that would be expected to comprise generally hard granules and that substantially is lacking granules and particles smaller than 150 or 125 micrometers.

U.S. Pat. No. 4,161,516 teaches a composition for treating airway disease using soft tablets or granules for inhalation administration. The method of the patent is suitable for producing granules that are soft enough to break apart in an airstream.

U.S. Pat. No. 6,752,939 teaches a method and an apparatus for predicting the suitability of a substance for dry granulation by roller compaction using small sample sizes.

U.K. Patent 1,558,153 discloses a method for producing organic dye material from finely divided particles by compressing said finely divided particles to produce a coherent mass of material, comminuting said coherent mass of material, and recovering granular material in the particle size range of 100-1000 microns from said comminuted material. The finest particles are removed by air flow.

We have now found an improved method of making granules and tablets. The method is applicable to a large variety of solid powder substances, e.g. APIs and excipients, as well as non-pharmaceutical products e.g. those used in the chemical and food industries.

BRIEF DESCRIPTION OF THE INVENTION

According to the invention, we provide a method for producing granules from a powder, wherein a low compaction force is applied to the powder to produce a compacted mass comprising a mixture of fine particles and granules and separating fine particles from the granules by entraining the fine particles in a gas stream.

The method will typically further comprise the step of collecting the granules. As explained below, the method may typically be run as a continuous process.

Suitably the process is carried out in the substantial absence of liquid.

The powder, e.g. the APIs and/or excipients usable in pharmaceutical industry, to be used in the granulation process of the invention, generally comprises fine particles. Further, the powder may typically have a mean particle size of less than 100, 50 or 20 micrometers. The fine particles in the powder may typically have a minimum particle size of 2, 5 or 10 μm and maximum size of 150, 100 or 75 μm. The inventors believe that the inventive ideas of the method disclosed herein may be applicable to form granules also from powder whose minimum particle size is smaller than the typical minimum size mentioned above, e.g. 0.001, 0.01 or 1 μm.

The mean particle size may be measured for example using a set of sieves. In case of very fine powders, also microscopy may be used for analyzing the particle sizes. The flowability of such powders is generally insufficient for e.g. tableting purposes. An exemplary method for determining sufficient flowability of a mass is disclosed in the detailed description of FIG. 9.

Hence "fine particles" or "fines" are individual particles typically having a mean particle size of less than 100, 50 or 20 micrometers and a maximum size of 150, 100 or 75 μm.

When several fine particles (e.g. 3, 5, 10 or more) agglomerate to form granules of maximum size of 150, 100 or 75 μm, they are referred to as small granules. Granules larger than the maximum size are referred to as "acceptable granules". Those granules that remain after fine particles and/or small granules have been entrained by the gas stream, are called "accepted granules".

The low compaction force may be provided for example using a roller compactor. The roller compactor may be accompanied by an optional flake crushing screen or other device, e.g. oscillating or rotating mill, suitable for producing granules from the compacted material. The optional step of employing a flake crushing screen or other device, will, if necessary, prepare the material for separation of fine particles and/or small granules from other granules.

Thus typically the compaction force is applied to the powder by a process comprising use of a roller compactor to generate a ribbon of compacted powder which is broken up to produce granules e.g. by means of a flake crusher. The flake crusher or similar device may permit the upper size of granules to be controlled e.g. by passing them through a screen. The aperture size of the flake crushing screen may be e.g. 0.5 mm, 1.0 mm or 1.2 mm.

The low compaction force may be adjusted to be at minimum such that at least one, five, ten or fifteen percent of the powder substance becomes acceptable granules during compaction and/or fractionating steps, while the rest of the material remains fine particles and/or small granules.

If the compaction force used is too low, inventors have observed that the granules accepted by the process may be too fragile for e.g. tableting purposes. Such granules may also be too large, e.g. larger than 3 mm. Fragile granules may not flow well enough or be strong enough to be handled e.g. in a tableting process.

The maximum low compaction force may be adjusted so that 75 percent or less, 70 percent or less, 65 percent or less, 50 percent or less or 40 percent or less, of the powder is compacted into acceptable granules and the rest remains as fine particles and/or small granules. The maximum low compaction force is typically up to 500%, 250% or 150% of a minimum low compaction force.

For instance, the compaction force may be sufficiently low that 75% or less by weight of the powder is compacted into acceptable granules having particle size larger than 150 μm (and/or a mean size of 100 μm or greater) and the rest remains as fine particles and/or small granules.

The maximum and minimum low compaction forces will of course depend on the particular compactor and powder used. Thus, for example the minimum low compaction force may be adjusted so that it is the minimum possible compaction force, 15 kN, 20 kN or 30 kN in a Hosokawa™ (Osaka, Japan) Bepex Pharmapaktor L200/50P roller compactor. The maximum low compaction force may also be adjusted so that it is 80 kN or less, 70 kN or less, 60 kN or less or 45 kN or less in a Hosokawa™ Bepex Pharmapaktor L200/50P roller compactor.

Typically a low compaction force is 60 kN or less e.g. 45 kN or less. Typically, a low compaction force is 16 kN or more.

The maximum low compaction force may also be adjusted so that substantially no solid bridges are formed in the granules of the resulting mass e.g. due to heating of the mass. Some compactors known in the art provide means for cooling the compacted material to alleviate the heating issues introduced by use of high compaction forces. With the method and system of the present invention, this precaution is unnecessary.

The compaction force may be adjusted using a method appropriate for the compactor employed, for example by control of the rate of feed into the compactor.

The gas stream may be provided by any suitable means, e.g. a suction fan. The gas stream, e.g. air, may be directed through a fractionating chamber. The gas stream separates at least some fine particles and/or small granules from the mass comprising acceptable granules, small granules and fine particles. The separated fine particles and/or small granules entrained in the gas stream may be transferred from the fractionating chamber to a separating device, e.g. a cyclone where the carrier gas is separated from the fine particles and/or small granules. The fine particles and/or small granules may then be returned to the system for immediate re-processing (i.e. they are re-circulated for compaction) or they may be placed into a container for later re-processing.

Thus, conveniently, fine particles and/or small granules are separated from the acceptable granules by means of an apparatus comprising fractionating means. Desirably, the fractionating means comprises a fractionating chamber.

As discussed in greater detail in the examples, the largest acceptable granules exiting from the fractionating chamber are usually larger in size than the largest granules entering the fractionating chamber. The inventors believe that a process whereby small granules and/or fine particles agglomerate with larger granules takes place during the conveyance of the material through the fractionating chamber.

Suitably the direction of the flow of the gas stream has a component which is contrary to that of the direction of flow of the compacted mass in general and accepted granules especially. Typically the direction of the flow of the gas stream is substantially contrary to (e.g. around 150-180° to), and preferably contrary to that of the direction of flow of the compacted mass.

The gas may, for example, be air (suitably dry air).

The fractionating means may comprise means to guide a gas stream into the fractionating means, means to put the compacted mass into motion and means to guide removed fine particles and/or small granules entrained in the gas stream from the fractionating means, e.g. for re-processing. The compacted mass may be put into motion simply by the effect of gravitation and/or by mechanical means.

A number of fractionating means are known which may be suitable for use in performance of the invention. The fractionating means may for example comprise a moving device e.g. a rotating device, such as a cylinder (or cone), along the axis of which the compacted mass is moved in the gas stream. Movement of the compacted mass may be by gravitational means or may be facilitated by mechanical means, or by features of the device (e.g. cylinder). The rotating device may comprise at least one structure for guiding the compacted mass inside the rotating device, such as by provision of a spiral structure. The spiral structure may be formed of channels or baffles which guide the movement of the compacted mass. A component of gravitational assistance or resistance may be provided by tilting the axis of the rotating device.

Advantageously the fractionating means does not require passage of the compacted mass through any sieve (such as a mesh screen). Sieves have a tendency to break up lightly compacted granules, therefore avoidance of use of a sieve permits lightly compacted granules, with their favorable properties, to be preserved e.g. for tableting. Moreover sieves are easily clogged, which disrupts the process, especially when run in continuous operation. Additionally, the eye size of a sieve may vary during the period of operation due to transient clogging.

The fractionating means may contain apertures through which fine particles and/or small granules are entrained. In one specific embodiment of the invention the gas stream enters the rotating device along its axis (in the opposite sense to movement of the compacted mass) and exits the rotating device through apertures (perforations) in the side walls of the rotating device.

As noted above, the fractionating means may comprise a moving device, e.g. a rotating device to move the compacted mass in the fractionating means. The moving device may comprise apertures through which the gas stream flows into and out of the moving device and through which the fine particles and/or small granules are entrained. The apertures through which gas flows out of the device may be substantially larger than rejectable fine particles, e.g. at least 50%, 100% or 150% of the average diameter of accepted granules. In absolute terms, the apertures may for example have a minimum dimension of around 250 µm, 500 µm or 750 µm or more. This helps prevent the apertures from clogging even when relatively high volumes of fine particles of possibly sticky material need to be separated from the compacted mass. In this sense, the moving device significantly differs from an air sieve of the prior art where the sieve mesh size must be of about the same size as the largest rejected particle. Instead of relying on the mesh size in the sieving, the fractionating device of the invention relies on the gas stream's ability to entrain fine particles from the moving compacted mass. The determination of the size of acceptable granules is achieved by balancing their gravitational force (together with other forces, e.g. mechanical and centrifugal forces) against the force of the gas stream.

Some of the fine particles and/or small granules may be agglomerated to other granules in the fractionating means and/or in the pneumatic conveying means by means of the individual or combined influence of the carrier gas stream, mechanical forces, attractive forces and electrostatic forces, for example. Thus, the process may produce granules that are larger than what is produced by the flake crushing screen of the system. In some embodiments, the degree of agglomeration of the compacted mass in the fractionating phase may be significant.

The movement of the mass in the gas stream may be achieved by applying, for example, a mechanical force, gravitational force, centrifugal force or a combination of these. In some embodiments, a mechanically moving component in the fractionating means may not be needed at all to realize the benefits of the present invention. In some embodiments, the acceptable granules fall in a gas stream e.g. by effect of gravitation force and unacceptable particles and granules are moved to at least partially opposite direction by the gas stream.

Typically the average residence time of the compacted mass within the fractionating means is at least 2 seconds, perhaps even at least 5 seconds, although the desired fractionating effect (including any agglomerating effect) may be achievable also in a time frame shorter than that.

It should also be noted that the rejected fraction of the mass may also contain acceptable granules. By allowing some recycling of acceptable granules the overall apparatus may be made e.g. more efficient and easier to maintain as clogging of fractionating device may be more easily avoided. These rejected acceptable granules may be conveyed to the beginning of the granulating process along with the other rejected material for reprocessing. For efficiency, we prefer that at maximum 30, 45, 60 or 75 percent of acceptable granules are re-cycled with the fines. The inventors have not observed any detrimental effect on the granulate mass caused by recycling. This is attributable to the use of low compaction force.

According to a further feature of the invention we provide an apparatus comprising compacting means and means adapted to separate fine particles and/or small granules from a compacted mass by entraining the fine particles and/or small granules in a gas stream, e.g. air.

Thus an apparatus according to the invention may be characterized in that said fractionating means for example comprising a rotating device (see e.g. (401) in the drawings) comprises at least one exit aperture (see e.g. (511) in the drawings) through which said gas stream flows out of said means said aperture being large enough to allow a granule having acceptable properties (e.g. flowability, tabletability, size, especially size) to flow out of said device.

The apparatus may further comprise a separating means (e.g. a cyclone) to separate the gas stream from the particles removed from the compacted mass.

A further specific aspect of the invention provides an apparatus for dry granulation, characterized in that the apparatus comprises compacting means capable of producing low compaction force and fractionating means adapted to separate fine particles and/or small granules from a compacted mass by entraining the fine particles and/or small granules in a gas stream. The apparatus may suitably comprise a roller compactor to generate a ribbon of compacted powder which is then broken up to produce granules. Said apparatus may be characterized in that said fractionating means comprises means to move said compacted mass. Said means to move said compacted mass may comprise means to move said compacted mass by gravitational or mechanical means. An apparatus according to the invention may, for example, be characterized in that said fractionating means comprises at least one structure (see e.g. (403) in the drawings) for guiding said compacted mass inside said fractionating means.

An apparatus according to the invention may comprise means to provide the gas stream wherein the direction of the flow of the gas stream has a component which is contrary to that of the direction of flow of the compacted mass (e.g. the direction of the flow of the gas stream is substantially contrary to that of the direction of flow of the compacted mass).

An apparatus according to the invention is typically provided with a fractionating means which comprises a rotating device (e.g. a cylinder or cone, especially a cylinder) along the axis of which the compacted mass is moved in said gas stream. Movement of the compacted mass along the axis of the rotating device may be facilitated by means of a spiral structure which guides the movement of the compacted mass. The fractionating means e.g. the rotating device may contain apertures through which the fine particles and/or small granules are entrained. When it is desired to produce granules of mean size x, the apertures may have a minimum dimension of 0.5×, or 1.0× or even 1.5×. In absolute terms the apertures may, for example, have a minimum dimension of 250 µm, 500 µm or 750 µm.

The invention also provides a fractionating device adapted to separate fine particles and/or small granules from a compacted mass by entraining the fine particles in a gas stream which comprises a rotating device, such as a cylinder or cone, along the axis of which the compacted mass is moved in said gas stream and which rotating device contains apertures through which fine particles and/or small granules are entrained.

In one embodiment, the fractionating device comprises a fractionating chamber there being, mounted inside the chamber, an open ended cylinder (or cone). The open ended cylinder (or cone) may be rotatably supported on rollers. Carrier gas is supplied to the inside of the open ended cylinder (or cone). The jacket of the cylinder (or cone) may be perforated with apertures through which fine particles and/or small granules are entrained in the carrier gas. As described elsewhere, the entrained fine particles and/or small granules may be captured for recycling.

In the method and apparatus according to the invention, pneumatic transport may be used. Suitably, the gas used to entrain the fine particles in the compacted mass is in fluid communication with the carrier gas used to transport materials in continuous operation.

Thus, suitably the powder for compaction is conveyed from a reservoir to the means to apply compaction force by means comprising use of a pneumatic conveyor.

The pneumatic transport may use a device, e.g. a cyclone, for separating carrier gas from fine particles. The device may be for example capable of continuous operation at an about even gas flow rate, in the sense that the carrier gas stream used in the fractionating process is not disturbed by pressure changes, e.g. by pressure shocks, such as are required to keep filters of various types open.

"Continuous operation" in this context means ability to operate without maintenance or other interruptions for at least one hour, eight hours or 24 hours.

One aspect of the invention is a dry-granulate mass containing granules obtainable according to the method of the invention.

According to the invention, we also provide a granulate mass, wherein the granules may have a mean granule size of more than 50, 100, 200 or 500 micrometers, maximum granule size of 3, 2 or 1 millimeters and good flowability. The mass may alternatively or additionally have at least one, two, three or four of the following properties: substantial absence of solid bridges between particles within the granule, good homogeneity, porous structure of the granules, substantial proportion of small granules and/or fine particles in the mass (typically associated with other granules), good compressibility and tabletability. Suitably the granules have a mean granule size of more than 100 micrometers and a maximum granule size of 3 millimeters.

Further, without being limited by theory, the inventors believe that the product of the process of the invention is influenced by triboelectric effects caused by passage of powder through the system. It is suggested in prior art that small particles may have a tendency to develop a negative charge whereas larger particles develop a positive charge (or at least a less negative charge) (see e.g. article "Generation of bipolar electric fields during industrial handling of powders" by Ion. I. Inculet et al, Chemical Engineering Science 61 (2006), pages 2249-2253) e.g. when conveyed by a gas stream or otherwise moved in a gas stream. Thus, according to one envisaged embodiment of the invention, there is provided a dry-granulated granulate mass, characterized in that it contains granules having typically a mean size of between 50 μm and 3 mm. (e.g. between 100 μm and 3 mm) consisting of (a) a compressed core containing fine particles of material associated by Van der Waals forces; and (b) a coating layer containing fine particles and/or small granules of said material associated with said compressed core by electrostatic forces. According to another envisaged embodiment of the invention there is provided a dry-granulated granulate mass, characterized in that it contains granules having a mean size of between 50 μm and 3 mm (e.g. between 100 μm and 3 mm) consisting of (a) a compressed core containing fine particles of material associated by Van der Waals forces; and (b) a porous coating layer containing fine particles and/or small granules of said material. In one embodiment, the coating layer (b) contains mostly, e.g. 70, 80 or 90%, fine particles as opposed to small granules. In another embodiment, the coating layer (b) contains mostly, e.g. 70, 80 or 90%, small granules as opposed to fine particles.

Suitably the compressed core is substantially free of solid bridges.

Such a dry granulate mass may also be characterized in that the mean particle size of the particles of material is 1-100 μm, the mean size of the compressed core is 50-3000 μm, and the ratio of the mean particle size of the fine particles and/or small granules of material of the coating layer to the mean size of the compressed core is at least 1:10, e.g. at least 1:30.

Most desirable characteristics of the granulate mass are typically good flowability, good tabletability, good homogeneity, porous structure of the granules, substantial proportion of small granules in the mass and substantial absence of fine particles in the mass.

To analyze particle size of a granulate mass, a stack of for example four sieves may be used where opening sizes of the sieves are for example 850 μm, 500 μm, 250 μm and 106 μm.

The mean granule size of material accepted by fractionating means may be calculated as the geometric mean of the diameter openings in two adjacent sieves in the stack.

$$d_i=(d_u \times d_o)^{0.5}$$

where $d_i$=diameter of $i^{th}$ sieve in the stack $d_u$=diameter opening through which particles will pass (sieve proceeding $i^{th}$)

$d_o$=diameter opening through which particles will not pass ($i^{th}$ sieve).

Because it is not practical to count each particle individually and calculate an average, the average particle size can be calculated on a weight basis. This can be done for example with the following equation:

$$d_{gw}=\log^{-1}[\Sigma(W_i \log d_i)/\Sigma W_i]$$

The standard deviation can now be calculated as follows:

$$S_{gw}=\log^{-1}[\Sigma W_i(\log d_i - \log d_{gw})^2/\Sigma W_i]^{0.5}$$

More detailed description of the exemplary size analysis method shown here is available in an article "Scott Baker and Tim Herrman, Evaluating Particle Size, Kansas State University, May 2002."

It should be born in mind that when the particle size of the granulate mass is analyzed by the above method, at least some of the coating particles/small granules may be detached from the compressed core.

Flow characteristics, e.g. good flowability, may be determined using an open-ended cone having a round opening in the narrower end of the cone, e.g. a filter funnel. One set of such cones and related test method is described in more detail with respect to FIG. 9.

Substantial absence of solid bridges in the granule structure means for example structure where less than 30% or 10% of particles of the granule are kept together with solid bridges on average. Presence of solid bridges in the granule structure may be analyzed for example using a scanning electron microscope. With such device, it may be possible to identify individual fine particles in the granulate structure as well as visible solid bridges such as crystallized structures between the particles of the granule.

Good homogeneity in this context may mean for example a granulate mass that consists of granules whose standard deviation from mean granule size is less than 2.5, less than 2.25 or less than 2.0. Inventors further believe that the homogeneous characteristics of the granulate mass of embodiments of the invention may have at least partially be achievable by the porous structure of the granules. Because of the homogeneous characteristics of the mass, the mass may be conveyed in the manufacturing process without any significant segregation of material. Yet further, good homogeneity of the granular mass may contribute to the good tabletability of the mass e.g. as demonstrated by less susceptibility to the capping phenomenon.

The structure of the accepted granules, and especially a coating layer, may be generally porous, i.e. dense granules may be substantially absent in the granulate mass. The core of the granule is expected to be porous due to the use of low compaction force. Porous structure of the granule may alternatively or additionally mean, for example, that the surface of the granule may be observed to comprise pores and/or loosely attached small granules and/or fine particles of size of approximately at least 1, 2 or 5 micrometers and less than 150, 100 or 50 micrometers. For example images about granules having porous structure, see FIGS. 2d, 2e and 2f.

Substantial absence of dense granules means that less than 20 or 10 percent of the resulting mass weight is dense granules. Dense granule is e.g. a granule whose surface appears to be a compressed, non-porous one (see e.g. FIG. 2c).

The granulate mass may also comprise a substantial proportion of small granules and/or fine particles, possibly forming a coating layer on larger granules which is loosely attached e.g. via electrostatic forces. A substantial proportion of small granules and/or fine particles may be more than 2%, 5% or 10% of the overall weight of the granulate mass.

Presence of small, preferably porous granules and/or fine particles may contribute positively e.g. to the flowability and compressibility of the granulate mass. This may for example lead to an improved tensile strength and/or more rapid disintegration time of a tablet compressed from the granulate mass. Surprisingly, and contrary to what is taught in the prior art, e.g. in WO99/11261, the substantial proportion of small granules and/or fine particles in the granulate mass of the invention does generally not seem to affect the flowability of the granulate mass in any significant negative manner.

The inventors have also discovered that, at least in some cases, if granules obtained by the process of the invention are taken and a proportion of the starting material composed of fine particles is added back (eg up to 15% fine particles is added back to a granulate mass that may already have e.g. 20% of fine particles and/or small granules, e.g. mass of "flowability example 3") then the homogeneity, flowability and tabletability of the granulate mass is not adversely affected in a significant manner. The added fines are, perhaps, taken into the porous surface of granules formed by the process of the invention. Inventors thus believe that in some embodiments, it may be possible to use granules of some embodiments of the invention as "carrier granules" that may absorb e.g. into the pores of the granules up to 10%, 20%, 30% or more of fine particles and/or small granules comprising same or different material as the carrier granules. The flowability of such mixture may be at an excellent, very good or good level.

The granulate mass is believed to have good compressibility because at least the surface of the granules is porous. The compressibility of the granulate mass of the invention may be good, i.e. it may have a Hausner ratio of greater than 1.15, 1.20 or 1.25. The low compaction force of the present invention may be adjusted so that the compressibility as indicated by the Hausner ratio stays at good level. The Hausner ratio may be calculated using formula $p_{tap}p_{bulk}$ where $p_{tap}$ represents tapped bulk density of the granulate mass and $p_{bulk}$ represents the loose bulk density of the granulate mass. The bulk densities may be measured by pouring 50 mg of granulate mass into a glass cylinder (e.g. make FORTUNA, model 250:2 ml) having an inner diameter of 3.8 mm. After pouring the mass into the cylinder, the volume of the mass is observed from the scale of the glass cylinder and loose bulk density of the mass is calculated. To measure the tapped bulk density, the glass cylinder is tapped 100 times against a table top using a force comparable to a drop from the height of 5 cm. The volume of the tapped mass is observed from the scale of the glass cylinder and tapped bulk density of the mass is calculated.

Surprisingly, and contrary to what is taught in the prior art, e.g. in WO99/11261, the compressibility of the granulate mass of the invention does not generally exhibit any negative influence on the flowability of the granulate mass. For example, a granulate mass of an embodiment of the invention with Hausner ratio above 1.25 generally exhibits very good or excellent flow characteristics.

Porous, well-flowing granules are generally desired in the pharmaceutical industry for example because it is possible to produce enhanced tablets from porous granules. Such tablets may for example disintegrate substantially quicker than tablets manufactured from dense granules. Further, tablets compressed from porous granules often show higher tensile strength than tablets compressed from dense granules. High tensile strength is often desirable for tablets as such tablets are easier to package and transport than fragile tablets.

The granulate mass may be tabletable so that using standard tableting techniques, e.g. using tableting forces available in widely used tableting machines, it is possible to form it into tablets having tensile strength of at least 5N, 10N or 15N. Tensile strength may be measured for example using a measuring device of make MECMESIN™ (Mecmesin Limited, West Sussex, UK) and model BFG200N.

The granulate mass may comprise at least one API and/or at least one excipient usable in pharmaceutical products. In one embodiment the granulate mass comprises (eg consists of) at least one (eg one) API. In another embodiment the granulate mass comprises at least one (eg one) API and at least one (eg one) excipient.

Thus the invention also provides a process for preparing a tablet which comprises compressing a dry-granulated granulate mass according to the invention optionally blended with one or more additional excipients. Said one or more additional excipients typically comprises a lubricant e.g. magnesium stearate. A tablet obtainable by such a process is another aspect of the invention.

According to the yet further feature of the invention we provide a tablet comprising dry-granulated granules. The tablet is characterized in that the tablet may have substantial absence of solid bridges binding particles within the granules forming the tablet. Alternatively or further, the tablet may have at least two or three of the following properties: high tensile strength, high drug load, low amount of lubricant, quick disintegration time and insensitivity to storage time.

Insensitivity to storage time may mean for example that the weight gain of the tablet in comparison to a new tablet is less than 2.0%, 1.5% or 1.0% after the tablet has been stored for four months in temperature of 40 degrees Celsius and in the relative humidity of 75%.

High drug load means that, for example the tablet may comprise at least 40 percent, 60 percent or 80 percent of API(s) of the overall weight of the tablet.

Quick disintegration time may be less than 600, 120 or 30 seconds when a tablet is put into water of approximately body temperature (i.e. 37 degrees Celsius).

As may be seen from the examples, tablets of the invention which have high tensile strength may nevertheless be capable of quick disintegration in water.

High tensile strength of the tablet may be more than 100N, 60N, 30N or 15N, e.g. as measured by MECMESIN™ BFG200N device.

A low amount of lubricant may be less than 1.0%, 0.5%, 0.3% or 0.2% of the weight of the tablet. It is known in the art that lubricant material such as magnesium stearate often has detrimental effect on tensile strength, disintegration time and/or dissolution time of a tablet. When mixing lubricant with granules of the prior art, the lubricant material may have a tendency to form a film around the (dense) granules, for example. The film may prevent formation of proper bonds between granules during tableting. (See e.g. article "A coherent matrix model for the consolidation and compaction of an excipient with magnesium stearate" by K. A. Rietma et. al., International Journal of Pharmaceutics, 97 (1993), pages 195-203.) Use of a low amount of lubricant with the granules of the present invention may thus contribute positively to the tensile strength and disintegration time of the tablet. The inventors speculate that the possibly soft and porous surface of the granule of the invention may prevent the formation of such films because the granules may have a larger, more uneven surface available for the lubricant to associate with. Thus the properties of the resulting tablet may be further improved.

The lubricant may be distributed essentially on the porous surface of the granules of the tablet. The lubricant may for example be located essentially on the surface and in the pores of the surface of the granules forming the tablet whereas there is no or little lubricant inside the core of the granule. The lubricant may be distributed e.g so that more than 90, 80 or 70 percent of lubricant is located in a cross-sectional area (cut surface) that is less than 10, 20 or 30 percent of the total sectional area of a tablet. The location of the lubricant particles on a sectional area of a tablet may be observed using e.g. a system comprising scanning electron microscope and additional equipment capable of identifying especially the particles comprising lubricant material.

The tablet may suitably exhibit substantially low percentage of hydrogen bonding liquid, e.g. water.

A tablet suitably exhibits substantially low percentage of liquid and/or hydrogen bonds, lubricant is unevenly distributed across the tablet and the tablet has further at least two of the following properties: quick disintegration time, high tensile strength, high drug load and low amount of lubricant.

The tablet of the invention may comprise excipient that comprises dry-granulated starch. For example it may comprise excipient that comprises up to 60% of dry-granulated starch.

A granulate mass or tablet of the present invention may typically comprise at minimum 1, 5 or 10 percent (weight) and at maximum 100, 95, 90, 80 or 70% of at least one active pharmaceutical ingredient. In some embodiments said powder contains an amount of active pharmaceutical ingredient of at least 60% e.g. at least 80%. The granulate mass or tablet may further comprise at minimum 5, 10, 20 or 30% (weight) and at maximum 99, 95 or 90% of at least one excipient, e.g. long-chain polymer e.g. starch or cellulose.

To control the disintegration and dissolution time of a tablet of the present invention, up to 90, 70 or 50 percent (weight) of e.g. metholose or hypromellose (hydroxypropyl methylcellulose) may be added to the formulation. The dissolution time of such tablet may be at least 1, 4, 8 or 12 hours in the gastric system.

The dissolution profile of a formulation comprising e.g. hypromellose may be for example such that after about 2 hours, from about 12% to about 60% of the API(s) is released; after about 4 hours, from about 25% to about 80% of the API(s) is released; after about 8 hours, from about 50% to about 100% of the API(S) is released; after about 12 hours, more than about 75% of the API(s) is released.

To achieve quick disintegration time for a tablet that comprises at least 5, 20 or 30 percent (weight) of at least one active pharmaceutical ingredient, the tablet may further comprise at minimum 1, 3 or 5 percent and at maximum 7, 10 or 20 percent (weight) of disintegrant. In some embodiments, the percentage of disintegrant in a tablet may be also higher than 20 percent. The disintegrant may be e.g. some starch or carboxymethyl cellulose (CMC, e.g. Nymcel™) or a combination of these. The granulate mass or tablet may also comprise at minimum 1, 5 or 10 percent and at maximum 60, 80 or 94% (weight) of filler (diluent), e.g. microcrystalline cellulose. The API, disintegrant and filler may be granulated together or separately using the method of the present invention.

For improving taste of e.g. a fast disintegrating tablet (orally disintegrating tablet), up to 50, 70 or 90% of sweetener, e.g. xylitol may be included into the tablet. If necessary, the sweetener may be granulated using an embodiment of the method of present invention. Further, the sweetener may be granulated separately or together with at least one other component (API or excipient) of a formulation. We have observed that at least with some APIs, use of separately granulated sweetener (xylitol) in a tablet may result as a quicker release time in comparison to a tablet where sweetener is granulated together with other components.

The tablet of the invention may have good content uniformity. For example, the standard deviation of the weight of the tablet may be less than 3.0%, 2.0% or 1.0% of the average weight of the tablets.

The granulation method and apparatus of the invention can be applied for many purposes in the pharmaceutical, chemical and food industries. The method and apparatus use low compaction force and gas stream to form granules of desired properties. The compaction force may be adjusted so that introduction of solid bridges is substantially avoided in the compaction step. The method and apparatus are adapted to treat the product granules gently to avoid breaking them, to separate fine particles and/or small granules from the acceptable granules, and optionally to re-circulate the rejected material for re-processing in the system. The apparatus and method can be made easily adjustable, controllable and more or less continuously operable.

The size distribution and/or flowability of the granules produced by the apparatus may be analyzed in real-time and the size distribution of the granules may be adjusted based on the analysis. For example, the flake crushing screen (see FIGS. 1a and 1b below) may be such that the aperture size of the mesh used for flake crushing can be varied by using some adjustment means. Another adjustable parameter typically is the gas flow rate of the fractionating device.

The method can be made economic as it allows re-processing of rejected material with practically no waste, and can be adapted to provide fast treatment of large amounts of material. The apparatus of the present invention may be adapted to be easy to clean and assemble and the process may be adapted to be stable and predictable thus making it easy to control.

Because of, for example, the homogeneity and/or flowability of the resulting granules, issues related to segregation can be avoided. The method of the present invention can be used in both small and large scale applications. Thus, when a product, e.g. granules or a tablet containing API(s) has been successfully developed under laboratory conditions, the time required to set up a validated large-scale manufacturing process can be short.

Because the method and apparatus of the present system is capable of granulating a variety of powders, including those consisting of 100% APIs, it is possible to produce granulate mass from separate substances in separate granulation processes and mix the resulting granules together after their individual granulations. Granulating API and excipients separately before blending may be advantageous e.g. when raw materials have very different particle sizes.

Different kinds of end products, including tablets, oral suspensions and capsules may be manufactured from the granulate mass.

According to the invention, we also provide a process for manufacture of a tablet which comprises tableting a granule according to the invention, or a granule made using the method of the invention.

We have found that the method of the present invention may be used for producing granules of large variety of powder substances usable in pharmaceutical industry.

The method of the present invention may thus be applicable to producing granules and tablets of the invention from material comprising APIs of one or multiple classes of APIs, the classes including for example antipyretics, analgesics, antiphlogistics, hypnosedatives, antihypnotics, antacids, digestion aids, cardiotonics, antiarrhythmics, antihypertensives, vasodilators, diuretics, antiulcers, antiflatulents, therapeutic agents for osteoporosis, antitussives, expectorants, antiasthmatics, antifungals, micturition improvers, revitalizers, vitamins and other orally administered agents. APIs can be used singly or two or more of them can be used in combination.

The method of the present invention may also be applicable to producing granules and tablets of the invention from material comprising specific APIs, for example paracetamol, acebutolol, metformin, fluoxetine, aspirin, aspirin aluminum, acetaminophen, ethenzamide, sazapirin, salicylamide, lactyl phenetidine, isothipendyl, diphenylpyraline, diphenhydramine, difeterol, triprolidine, tripelennamine, thonzylamine, fenethazine, methdilazine, diphenhydramine salicylate, carbinoxamine diphenyldisulfonate, alimemazine tartrate, diphenhydramine tannate, diphenylpyraline teoclate, mebhydrolin napadisylate, promethazine methylene disalicylate, carbinoxamine maleate, chlorophenylamine dl-maleate, chlorophenylamine d-maleate, difeterol phosphate, alloclamide, cloperastine, pentoxyverine (carbetapentane), tipepidine, dextromethorphan hydrobromide, dextromethorphan phenolphthalinate, tipepidine hibenzate, cloperastine fendizoate, codeine phosphate, dihydrocodeine phosphate, noscapine, dl-methylephedrine saccharin salt, potassium guaiacolsulfonate, guaifenesin, caffeine, anhydrous caffeine, vitamin B1 and derivatives thereof, vitamin B2 and derivatives thereof, vitamin C and derivatives thereof, hesperidin and derivatives thereof and salts thereof, vitamin B6 and derivatives thereof and, nicotinamide, calcium pantothenate, aminoacetate, magnesium silicate, synthetic aluminum silicate, synthetic hydrotalcite, magnesium oxide, aluminum glycinate, coprecipitation product of aluminum hydroxide/hydrogen carbonate, coprecipitation product of aluminum hydroxide/calcium carbonate/magnesium carbonate, coprecipitation product of magnesium hydroxide/potassium aluminum sulfate, magnesium carbonate, magnesium aluminometasilicate, ranitidine, cimetidine, famotidine, naproxen, diclofenac, piroxicam, azulene, indometacin, ketoprofen, ibuprofen, difenidol, promethazine, meclizine, dimenhydrinate, fenethazine tannate, diphenhydramine fumarate, scopolamine hydrobromide, oxyphencyclimine, dicyclomine, metixene, atropine methylbromide, anisotropine methylbromide, scopolamine methylbromide, methylbenactyzium bromide, belladonna extract, isopropamide iodide, papaverine, aminobenzoic acid, cesium oxalate, aminophylline, diprophylline, theophylline, isosorbide dinitrate, ephedrine, cefalexin, ampicillin, sucralfate, allylisopropylacetylurea, bromovalerylurea, and where appropriate (other) pharmaceutically acceptable acid or base addition salts thereof (e.g. those salts which are in common usage) and other such pharmaceutically active ingredients described in European Pharmacopoeia, $3^{rd}$ Edition and one, two or more of them in combination.

The method of the present invention may also be applicable to producing granules and tablets of the invention from material comprising solid APIs that may be poorly water-soluble, such as for example antipyretic analgesic agents such as benzoic acid, quinine, calcium gluconate, dimercaprol, sulfamine, theobromine, riboflavin, mephenesin, phenobarbital, thioacetazone, quercetin, rutin, salicylic acid, pyrabital, irgapyrin, digitoxin, griseofulvin, phenacetin, nervous system drug, sedation narcotics, muscle relaxant, hypotensive agent, antihistamines, antibiotics such as acetylspiramycin, erythromycin, kitasamycin, chloramphenicol, nystatin, colistin sulfate, steroid hormones such as methyltestosterone, progesterone, estradiol benzoate, ethinylestradiol, deoxycorticosterone acetate, cortisone acetate, hydrocortisone, prednisolone, non-steroid yolk hormones such as dienestrol, diethylstilbestrol, chlorotrianisene, other lipid soluble vitamins, and where appropriate (other) pharmaceutically acceptable acid or base addition salts thereof (e.g. those salts which are in common usage) and other such pharmaceutically active ingredients described in European Pharmacopoeia, 3$^{rd}$ Edition and one, two or more of them in combination.

The active pharmaceutical ingredient may, for example, be selected from acebutolol HCl, fluoxetine HCl, paracetamol, sodium valproate, ketoprofen and metformin HCl.

The method of the present invention may also be applicable to producing granules and tablets of the invention from material comprising excipients or other ingredients usable in e.g. pharmaceutical industry, such as for example L-asparagic acid, wheat gluten powder, acacia powder, alginic acid, alginate, alfa-starch, ethyl cellulose, casein, fructose, dry yeast, dried aluminum hydroxide gel, agar, xylitol, citric acid, glycerin, sodium gluconate, L-glutamine, clay, croscarmellose sodium, Nymcel™, sodium carboxymethyl cellulose, crospovidone, calcium silicate, cinnamon powder, crystalline cellulose-carmellose sodium, synthetic aluminum silicate, wheat starch, rice starch, potassium acetate, cellulose acetate phthalate, dihydroxyaluminum aminoacetate, 2,6-dibutyl-4-methylphenol, dimethylpolysiloxane, tartaric acid, potassium hydrogen tartrate, magnesium hydroxide, calcium stearate, magnesium stearate, purified shellac, purified sucrose, D-sorbitol, skim milk powder, talc, low substitution degree hydroxypropylcellulose, dextrin, powdered tragacanth, calcium lactate, lactose, sucrose, potato starch, hydroxypropylcellulose, hydroxypropyl methylcellulose phthalate, glucose, partially pregelatinized starch, pullulan, powdered cellulose, pectin, polyvinylpyrrolidone, maltitol, maltose, D-mannitol, anhydrous lactose, anhydrous calcium hydrogenphosphate, anhydrous calcium phosphate, magnesium aluminometasilicate, methyl cellulose, aluminum monostearate, glyceryl monostearate, sorbitan monostearate, medicinal carbon, granular corn starch, dl-malic acid and possibly other such others classified as excipient in Arthur H. Kibbe: Handbook of Pharmaceutical Excipients, 3$^{rd}$ Edition, and one, two or more of them in combination.

The method of the present invention may be applicable to producing granules and tablets of the invention from material comprising disintegrants such as for example carboxymethyl cellulose, Nymcel™, sodium carboxymethyl cellulose, croscarmellose sodium, cellulose such as low substitution degree hydroxypropylcellulose, starch such as sodium carboxymethyl starch, hydroxypropyl starch, rice starch, wheat starch, potato starch, maize starch, partly pregelatinized starch and others classified as disintegrators in Arthur H. Kibbe: Handbook of Pharmaceutical Excipients, 3$^{rd}$ Edition, and one, two or more of them in combination.

The method of the present invention may be applicable to producing granules and tablets of the invention from material comprising binders such as for example synthetic polymers such as crospovidone, saccharides such as sucrose, glucose, lactose and fructose, sugar alcohols such as mannitol, xylitol, maltitol, erythritol, sorbitol, water-soluble polysaccharides such as celluloses such as crystalline cellulose, microcrystalline cellulose, powdered cellulose, hydroxypropylcellulose and methyl cellulose, starches, synthetic polymers such as polyvinylpyrrolidone, inorganic compounds such as calcium carbonate and others classified as binders in Arthur H. Kibbe: Handbook of Pharmaceutical Excipients, 3rd Edition, and one, two or more of them in combination.

Examples of fluidizing agents include silicon compounds such as silicon dioxide hydrate, light silicic anhydride and others classified as fluidizing agents in Arthur H. Kibbe: Handbook of Pharmaceutical Excipients, 3rd Edition, and one, two or more of them in combination.

According to another aspect of the invention, we provide a granulate mass, characterized in that the mass is tabletable and has good flowability and that the mass comprises at least 10% of at least one of the following pharmaceutical ingredients:
acebutolol HCl,
fluoxetine HCl,
paracetamol,
sodium valproate,
ketoprofen and
metformin HCl.

According to another aspect of the invention, we provide a tablet, characterized in that the tensile strength of the tablet is at least 10N and the tablet is manufactured from dry-granulated granules comprising at least 10% (weight) of at least one of the following active pharmaceutical ingredients:
acebutolol HCl,
fluoxetine HCl,
paracetamol,
sodium valproate,
ketoprofen, and
metformin HCl.

According to another aspect of the invention, we provide a tablet formed by compression of a dry granulate mass comprising 60% or more (e.g. 70% or 80% or more) of active pharmaceutical ingredient selected from paracetamol, metformin HCl, acebutolol HCl and sodium valproate. The balance of the composition of the dry granulate mass may, for example be one or more disintegrants selected from starch, cellulose and cellulose derivatives. According to another aspect of the invention, we provide a tablet formed by compression of a dry granulate mass comprising (i) granules comprising 80% or more (e.g. 90% or more e.g. 100%) of active pharmaceutical ingredient selected from paracetamol, metformin HCl, acebutolol HCl and sodium valproate and (ii) granules comprising one or more disintegrants selected from starch, cellulose and cellulose derivatives. In either case a lubricant may optionally be blended with the dry granulate mass before compressing it into tablets.

In some embodiments, the tablets disintegrate in water of approximately body temperature, i.e 37 degrees Celsius, in less than 60 seconds. For quick disintegrating tablets, the API suitably does not exceed 95% of the tablet composition and the composition contains at least 2% of disintegrant. The tablets suitably have a tensile strength of greater than 40N. In one embodiment the tablets may comprise xylitol in an amount of 90% or less.

Some embodiments of the invention are described herein, and further applications and adaptations of the invention will be apparent to those of ordinary skill in the art.

BRIEF DESCRIPTION OF DRAWINGS

In the following, the invention is illustrated, but in no way limited by reference to the accompanying drawings in which

FIG. 2d shows an example of a granule according to an embodiment of the invention.

FIG. 2e shows another example of granules according to an embodiment of the invention, FIG. 2i shows surface images of granules produced using different low compaction forces according to embodiments of the present invention, FIG. 5a and FIG. 5b show two alternative exemplary cylindrical components that can be used in the fractionating device shown in FIG. 4.

DETAILED DESCRIPTION OF DRAWINGS

Figure 1A:
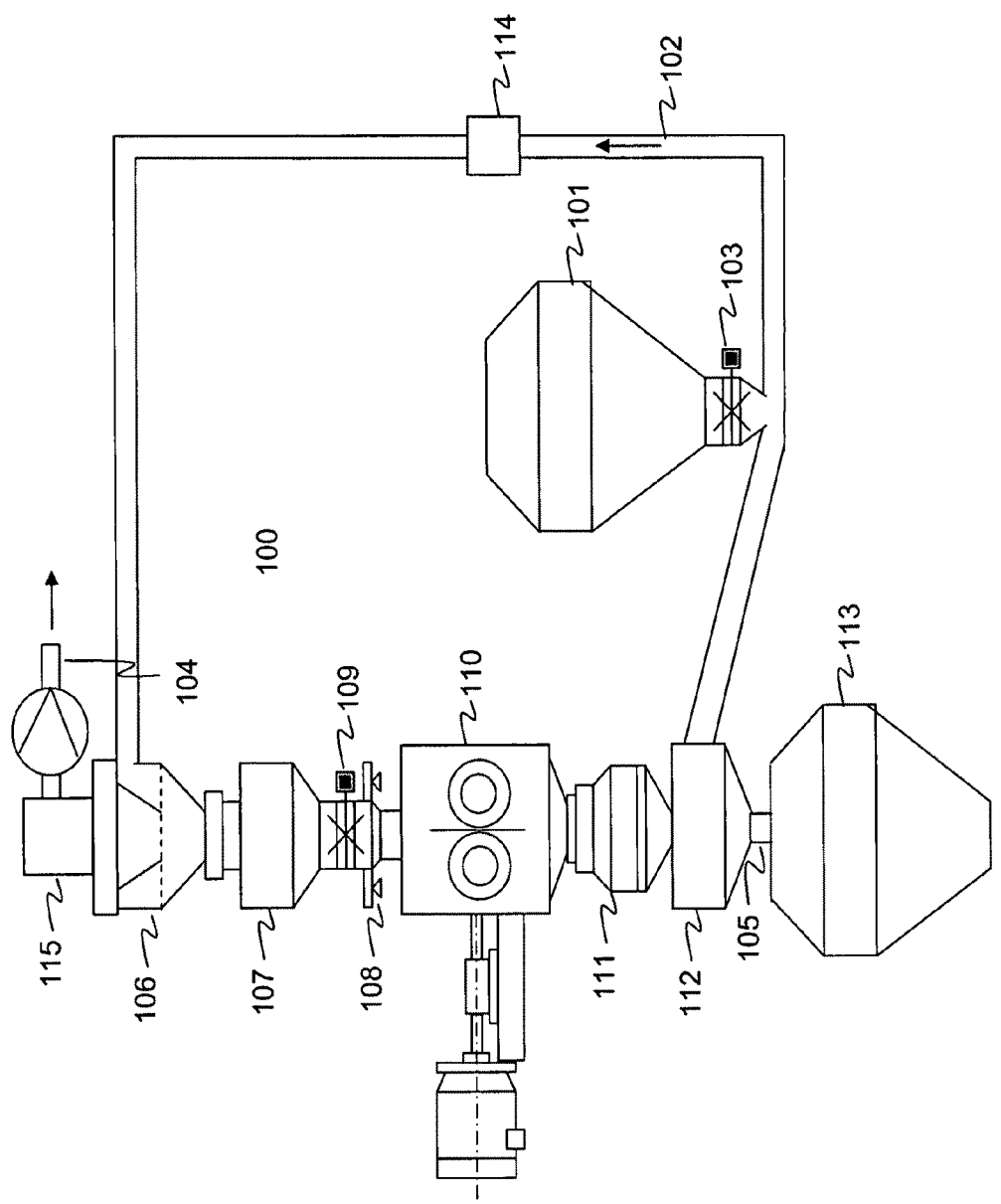
FIG. 1a and FIG. 1b show exemplary apparatus according to an embodiment of the invention.
Figure 1B:
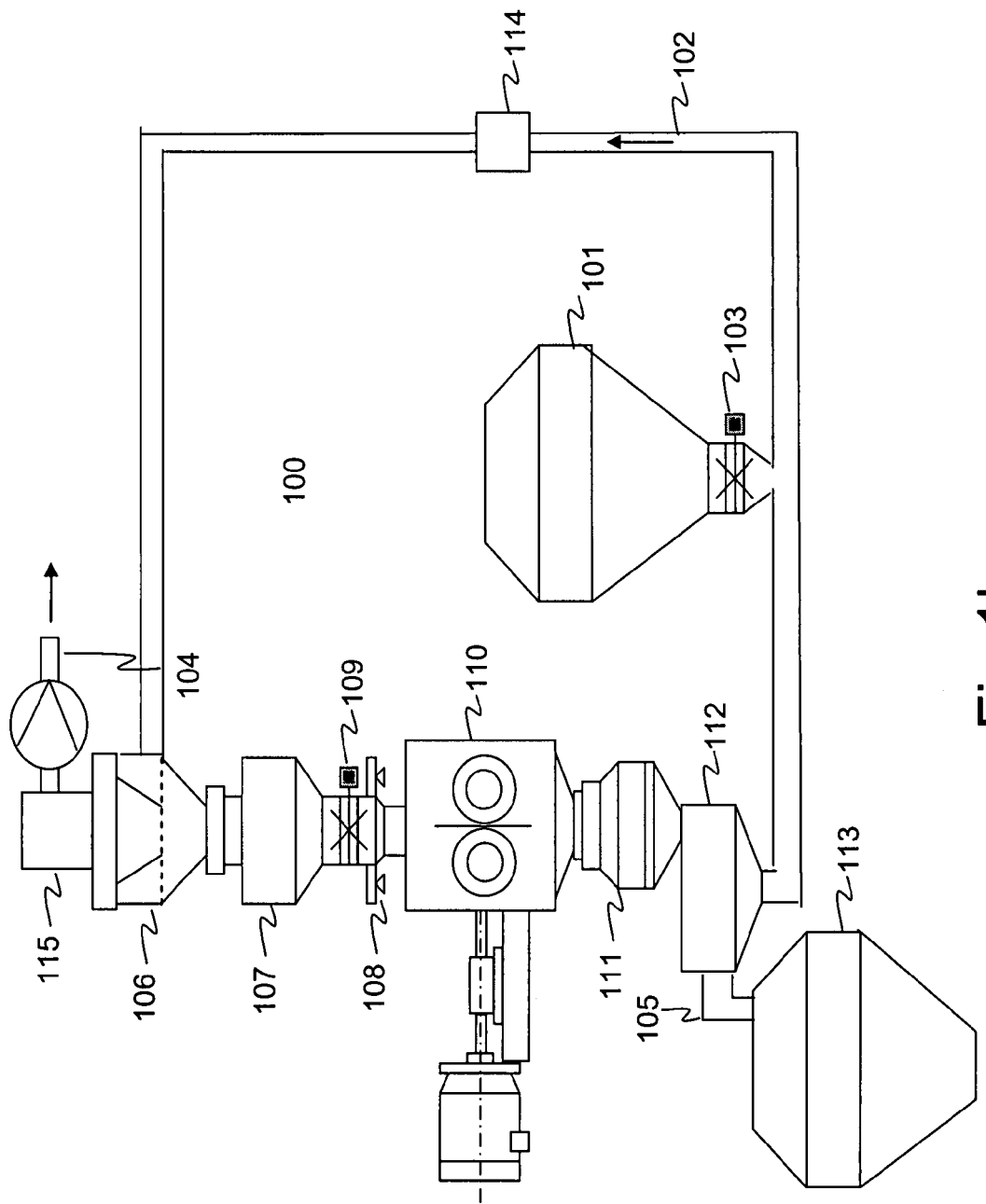

The apparatus 100 (FIGS. 1a and 1b) of an embodiment of the invention comprises a compacting device that compacts powder material into granules and a fractionating device that fractionates at least some fine particles and/or small granules away from acceptable granules. Two different alternatives for a fractionating device are shown in FIGS. 1a and 1b. The fractionating device 112 in FIG. 1a is shown in more detail in FIG. 3. The fractionating device 112 in FIG. 1b is shown in more detail in FIG. 4. The apparatus shown in FIG. 1a and FIG. 1b comprise a raw material feeding container 101, into which material to be granulated is fed. The feeding container is connected to a pneumatic conveyor pipeline 102, to which the material is passed through a feeder valve 103. The tubes of the pneumatic conveyor system have a diameter of about 47 mm and their material may be for example some suitable plastic material, e.g. polyethene. The feeder valve may be a so-called star-shape flap valve. One such valve is manufactured by Italian pharmaceutical device manufacturer CO.RA™ (Lucca, Italy). In operation, the closing element of the valve may be turned 180° alternately in either direction, whereby buildup of the powder substance in the container can be avoided. Other equipment intended for continuous charging of powder substance, such as compartment feeders, may also be used.

Figure 6:
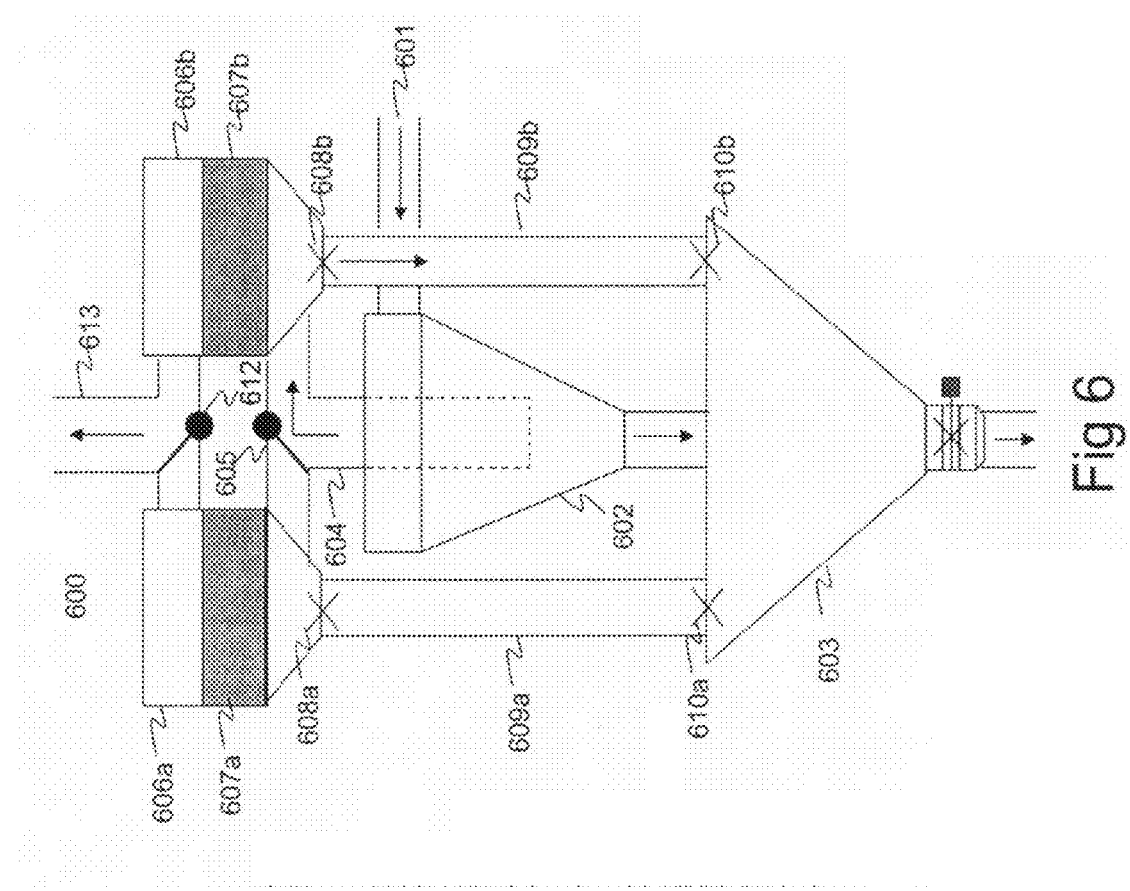
FIG. 6 shows an exemplary dual-filter arrangement for enabling continuous operation of the system of an embodiment of the present invention.

The pressure of the air flowing within the conveyor 102 may be adjusted to be lower than that of the surroundings. This may be achieved for example using an extractor suction fan 104. The suction fan is of make BUSCH™ (Maulburg, Germany) and model Mink MM 1202 AV. The fan may be operated for example at 1860 RPM. Makeup carrier gas may be supplied through a connection 105. The material fed from the feeding container is transported through the conveyor 102 into a separating device 106, wherein fine rejected particles and new feed from container 101 are separated from the carrier gas. The fan can be provided with filters (shown in FIG. 6) situated beside the separating device. The device may be capable of continuous operation. One such device is a cyclone. After the separating step, the separated powder falls into an intermediate vessel 107.

The container 107 can be mounted on load cells 108 to measure the weight of the material. The intermediate vessel 107 is provided with a valve 109 which may be of the same type as the feeding container valve 103. From the intermediate vessel 107, the powder is transferred to a compacting device, e.g. roller compactor 110 to produce a ribbon of compacted material which is then passed to a flake crushing screen 111 where granules are created by crushing the ribbon. In the context of this invention, compacting is considered as the step of the process that produces granules to be fractionated, regardless of whether a separate screen or milling device 111 is used or not. The compaction force of the compactor 110 may be adjusted by e.g. altering the feed rate of the powder substance, the rotating speed of the rolls of the roller compactor, the pressure applied to the rolls of the compactor device and/or the thickness of the resulting ribbon. The compaction force applied by the compactor may be adjusted to a low level to achieve the desired properties of the compacted mass, e.g. the porosity of the resulting granules and/or proportion of fine particles and/or small granules. The compactor and the flake crushing screen are devices well known to a person skilled in the art. After passing the compacting and flake crushing devices, the material is partially in the form of granules, but part of the material will still be in the form of fine particles and/or small granules. The maximum size of the granules as well as the mean size of the granules may be affected by, for example, the mesh size of the flake crushing screen. It should be noted, however, that size of a granule may increase as result of agglomeration in the fractionating and/or conveying steps of the process.

In some embodiments (not shown in figure), the apparatus 100 may comprise more than one compacting device, e.g. roller compactor, to improve e.g. capacity and/or continuous processing capabilities of the apparatus. The compacting devices may require some periodic service breaks e.g. for cleaning up. The apparatus 100 may continue operation even if one of the compacting devices is being serviced.

The product from the above steps that contains fine particles and porous granules and that may be statically charged (e.g. by triboelectrification) is conveyed to a fractionating chamber 112. There may be one or two e.g. star-shaped flap valves between compacting device and fractionating device to control the flow of compacted material to the fractionating device. The fractionating device divides the granulate mass into an accepted fraction and a rejected fraction on the basis of how different particles of the mass are affected by the carrier gas stream that flows in the fractionating device. The rejected fraction passes with the fed carrier gas stream to the feed conveyor 102, for re-processing, and the accepted fraction is led into a product container 113. By this means the product granules are treated gently and a relatively large volume of material comprising mostly fine particles and/or small granules is removed from the mass.

The operation of the fractionating chamber 112 is described in more detail with reference to FIGS. 3-6. There are many possible alternative fractionating devices.

In the embodiments shown in FIG. 1a and FIG. 1b, load cells 108 are fitted to the container 107. Such sensors and other instrumentation can also be arranged in other containers and components of the system. Not all of the possible instrumentation is shown in the figures. For example the pneumatic conveyor, if required, may be provided with at least one pressure difference sensor 114, the information from which can be used to control the operation of the apparatus.

The present invention may also be carried out as a batch process where the reject fraction is not immediately returned to the system using the conveyor 102, but fed into a container of reject material. Such a system is not described in detail, but its construction and use will be readily apparent to those of skilled in the art.

The apparatus can be automated by transferring information received from the various sensors e.g. the pressure difference sensors 114, the load cells 108 and the valves 103 as well as information regarding the speed of rotation and the loads of the motors to a control unit and by applying appropriate control logic and control circuits in a manner known to a person skilled in the art. Control of the compaction force of the compacting device, e.g. roller compactor is particularly useful, as granule structure as well as the proportion of fine particles and/or small granules is significantly affected by the compaction force used. The compaction force depends on a number of parameters, such as the rotating speed of the rolls and the feed rate of the powder substance. For example, the higher the feed rate of the powder substance for a given roller rotation rate, the higher the compaction force will be.

The material of the conveyor 102 may be e.g. PVC, e.g. FDA PVC. Various components of the system may be connected together with electric wires for grounding purposes. Suitably the entire system is grounded.

Figure 2A:
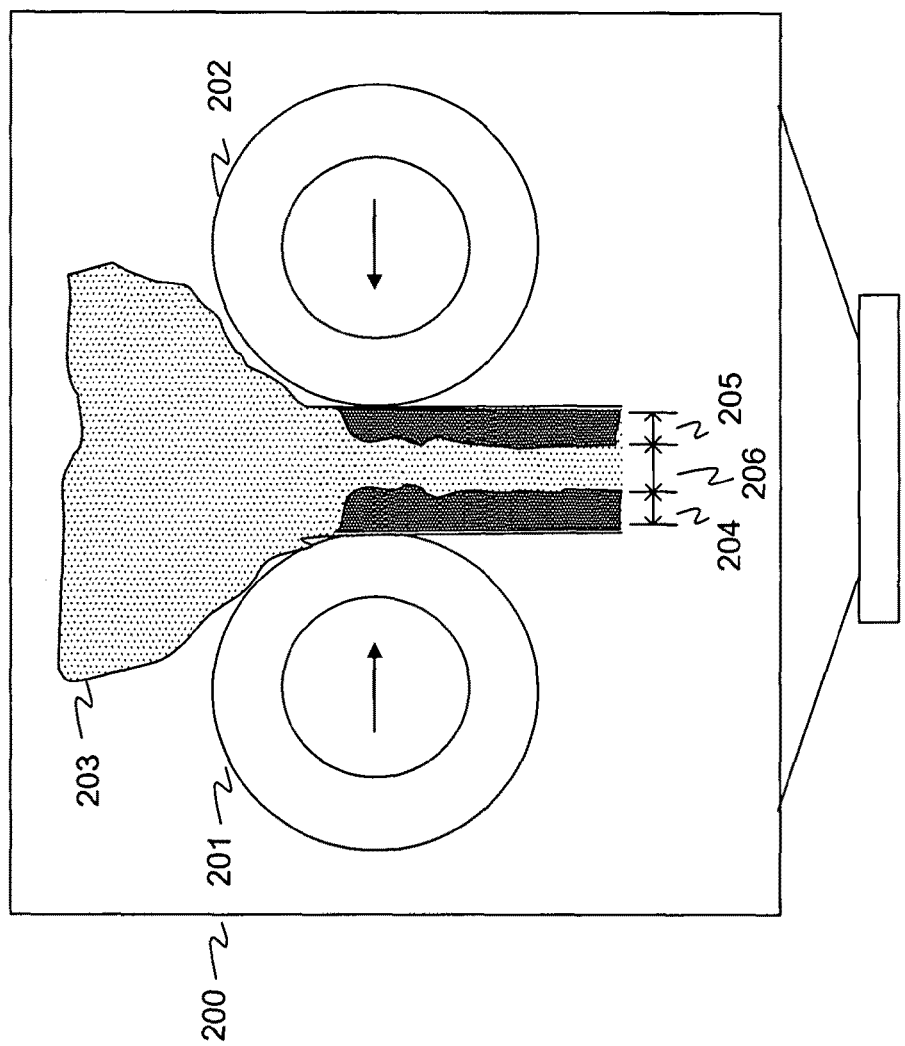
FIG. 2a shows use of roller compactor according to an embodiment of the invention.

In FIG. 2a the roller compactor 200 compacts the mass 203 containing raw material and optionally particles recycled from the fractionating device into a ribbon 204, 205, 206 using rolls 201,202 that apply mechanical force to the mass to be compacted. Depending on the compaction force applied to the mass and the thickness of the ribbon, the amount of mass that gets compacted into granules 204, 205 varies. The remaining mass 206 may remain small granules and/or fine particles example in the middle of the ribbon. The small granules and/or fine particles may not be capable of forming acceptable granules alone. However, the presence of such mass may have a positively contributing role in forming of acceptable granules in the fractionating and/or conveying steps of the process e.g. through triboelectrification and electrostatic forces. Depending on the feed material and compacting parameters, such as thickness of the ribbon, the proportion of fine particles and/or small granules may vary.

Figure 7:
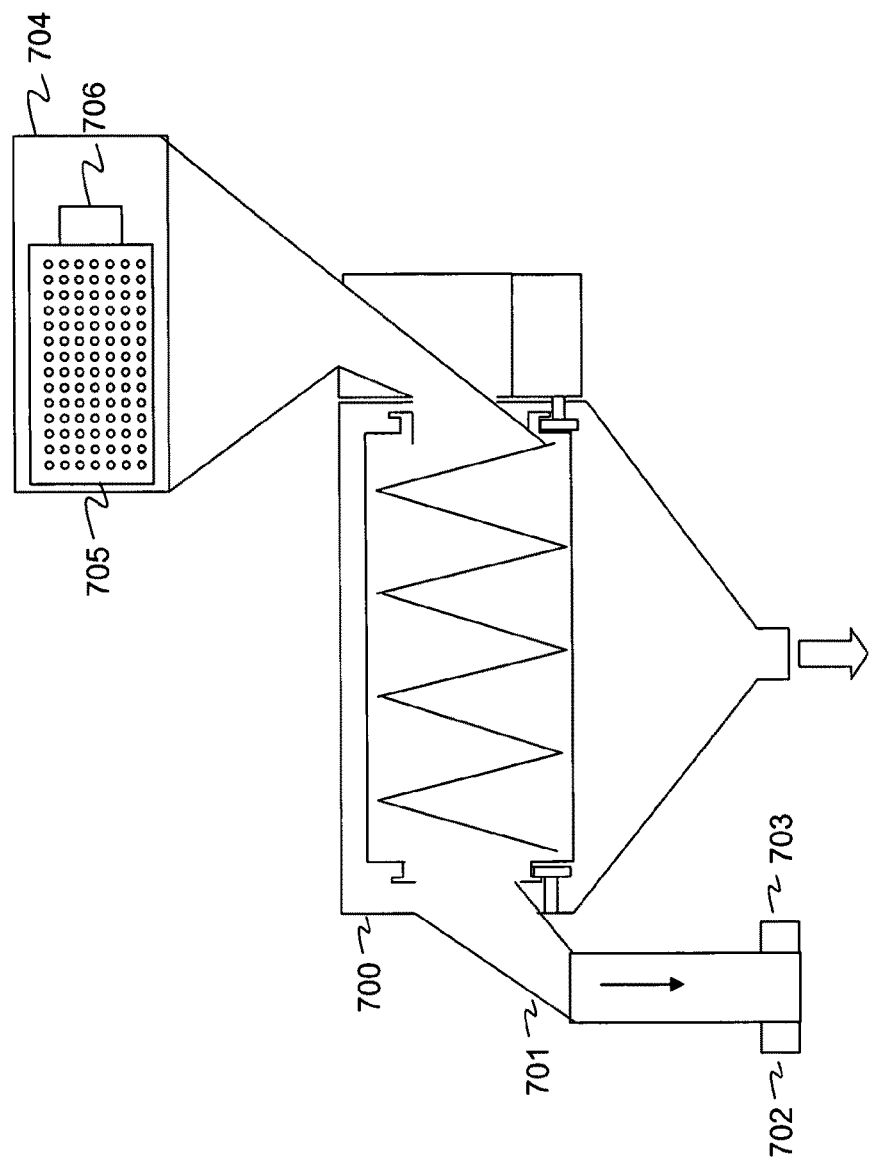
FIG. 7 shows an exemplary arrangement for monitoring and adjusting the characteristics of the accepted granules in real time.

A convenient way to adjust operating parameters of the system is to set the compaction force of the roller compactor to the minimum that produces at least some granules and set the rotating speed (see the description related to FIG. 4) of the fractionating device to the maximum available (e.g. about 100 RPM) in the device of make ROTAB™ (Donsmark Process Technology A/S, Copenhagen, Denmark) and model 400EC/200 and then adjust the carrier gas flow rate so that acceptable granules with desired flow characteristics start flowing out the system. Too little gas flow in the fractionating device causes the proportion of fine particles and/or small granules to increase in the mass of accepted granules whereas use of too high a gas flow causes a large proportion of acceptable granules to be unnecessarily re-processed. Setup of the optimal gas flow may be done manually or automatically for example using real-time measurement of flow of accepted granules and characteristics of those granules. One such measurement arrangement is shown in FIG. 7.

Figure 2B:
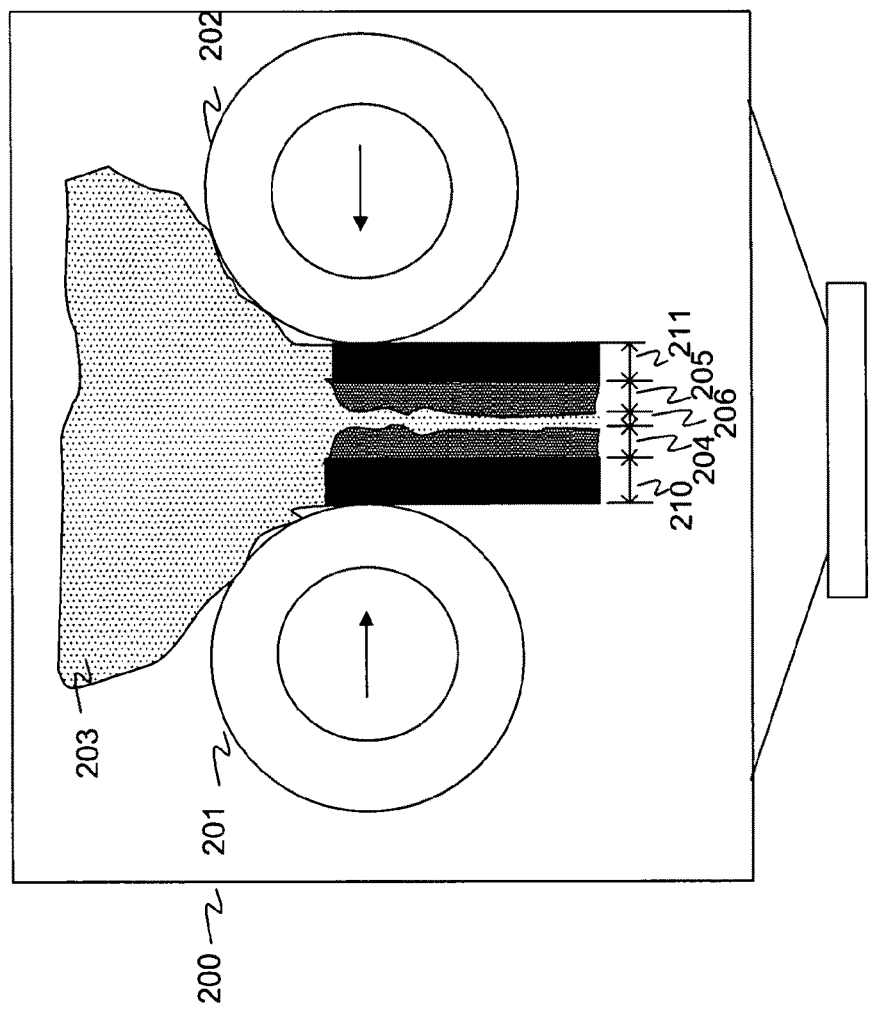
FIG. 2b shows use of roller compactor producing both avoidable dense (according to prior art) and desirable porous granules.

FIG. 2b illustrates an example of the creation of unwanted dense granules and/or granules having solid bridges 210, 211 when a high compaction force as in the prior art is used. The more dense granules there are in the mass, the lower the quality of the mass may be for tableting. Although the flow characteristics of the mass resulting from using prior art high compaction forces (or repeated compaction with lower forces) may be acceptable even without fractionating, the compressibility and/or tabletability of the mass may with some materials be significantly lower, or some other characteristics of the tablet such as disintegration time may be undesirable. Moreover, significant heating of the material in the compaction step of prior art granulation process may be observed leading for example to formation of solid bridges through crystallization and/or degradation of components of the granules or undesirable characteristics of the granulate mass. Yet further, use of high compaction force typically reduces the proportion of small granules and/or fine particles 206 in the resulting granulate mass. Too low a percentage of such small granules and/or fine particles in the fractionating and/or conveying steps of the process may adversely affect the quality of the resulting accepted granules.

Figure 2C:
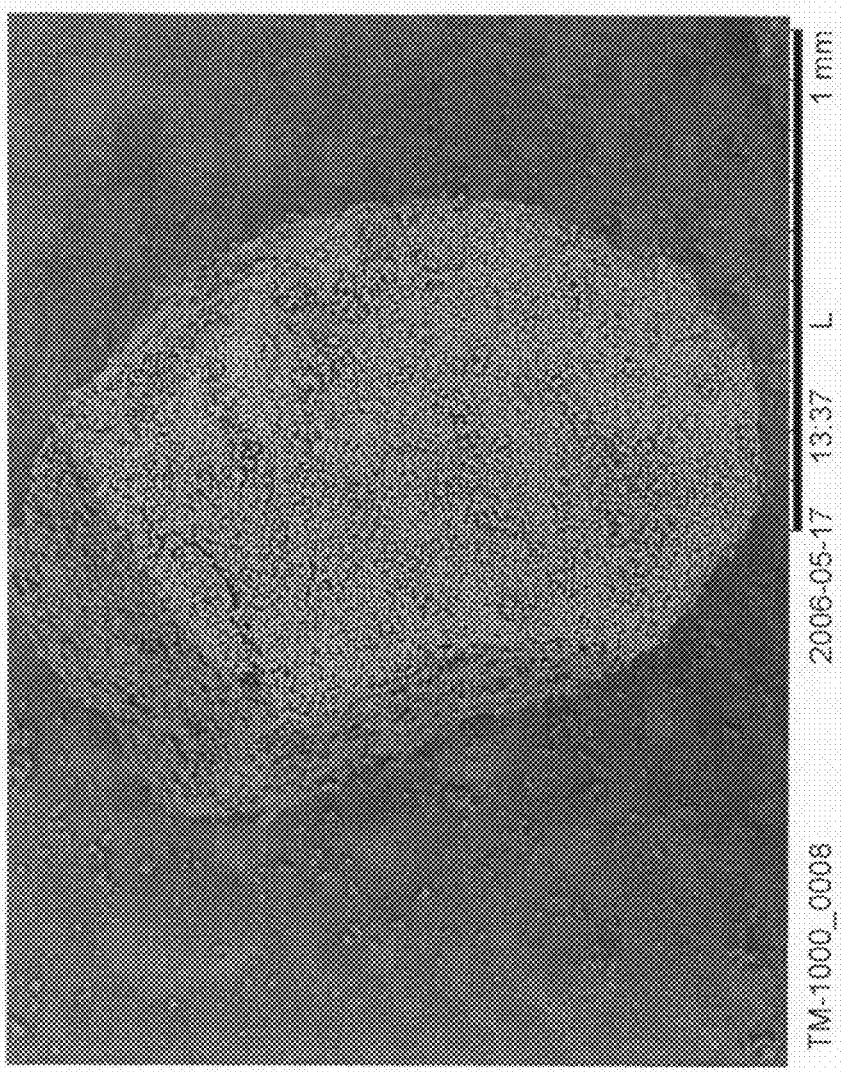
FIG. 2c shows an example of a granule produced by a method of prior art.

FIG. 2c shows a scanning electronic microscope (SEM) picture of an exemplary dense maize starch granule that is produced using high compaction force (e.g. more than 80 kN using Hosokawa Bepex Pharmapaktor L200/50P roll compactor) for maize starch (CERESTAR™ product code C*Gel 03401, batch number SB4944) typical of the dry granulation methods of the prior art.

FIG. 2d shows a picture of an exemplary porous starch granule of the same starch that is produced using low compaction force (in this case, 30-35 kN using the same Hosokawa roll compactor) and subsequent fractionation using gas stream according to an embodiment of the present invention. For different materials, the "low compaction force" that produces porous granules and "high compaction force" that produces unacceptable amount of dense granules and/or granules with solid bridges may vary. We have observed that the surface of the granule of FIG. 2c is less porous (i.e more dense) than the granule of FIG. 2d. There is more free space (i.e. pores) between the individual particles in the porous granule of FIG. 2d than in the dense granule of FIG. 2c. There also seems to be larger proportion of loosely attached particles on the surface of the porous granule of FIG. 2d than in the dense granule of FIG. 2d. Further, the granule of FIG. 2c has more edges than the granule of FIG. 2d. The round shape of the porous granule may contribute to the good flow characteristics of the granulate mass containing such granules. The pores between particles on the surface of the porous granule as shown in FIG. 2d may enhance the compressibility of the granule.

FIG. 2e shows another embodiment of granules of the present invention. Image 250 shows a plurality of 100% paracetamol granules 251 produced by the apparatus of an embodiment of the invention. Compaction force of 60 kN was used in the granulation process. According to our observation, paracetamol may be granulated using higher compaction forces than most other materials. Unless specified differently, the fractionating device used in the process of this and following examples is similar to the one described in FIGS. 4 and 5c. Typical size of a granule 251 in this sample is between 500 and 1000 μm. Image 252 shows a magnified picture of the surface of one of such granules. It may be observed from image 252 that the compacted surface 254 of the granule is covered mostly by small granules 255 (e.g. in the range of ca 5 μm-50 μm). Such individual small granules 257 are also shown in image 256. The small granules 255 are relatively loosely attached to the granule 251 forming a porous surface for the granule. Thus, although the compaction force used was higher than with typical materials, the surface of the resulting granules can be visually observed to be porous. Inventors contemplate that the small granules and/or fine particles may have been attached to the larger granules via electrostatic forces created e.g. by triboelectrification during the fractionating step of the process. The inventors contemplate further that the porous surface achieved via loosely attached small granules on the surface of the accepted granule may have a significant positive contribution to the flow and tabletability properties of the granulate mass.

Figure 2F:
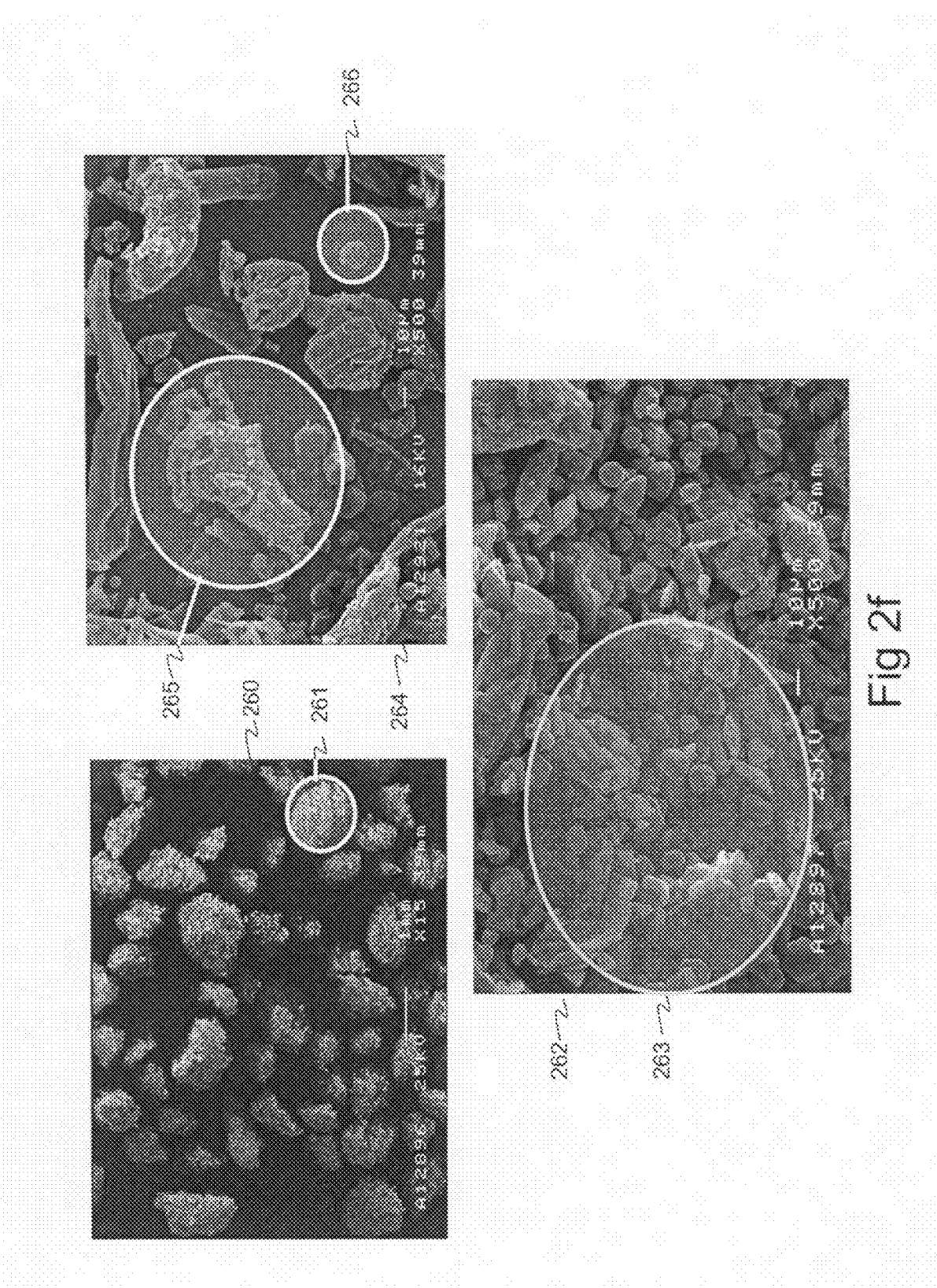
FIG. 2f shows yet another example of granules according to an embodiment of the invention.

FIG. 2f shows yet another embodiment of granules of the present invention. Image 260 shows a plurality of excipient granules 261 comprising 70% of microcrystalline cellulose and 30% of maize starch. A compaction force of 16 kN was used in the granulation process. Typical size of a granule 261 in this sample is between 500 and 1000 µm. Image 262 shows a magnified picture of the surface of one of such granules. It may be observed from image 262 that the compacted surface of the granule is covered by small granules and/or fine particles 263 (e.g. in the range of ca 5 µm-100 µm). Such individual small granules 265 and individual fine particles 266 are also shown in image 264. Small granules 265 and fine particles 266 are relatively loosely attached to the granule 261 forming a porous surface for the granule. The proportion of small granules (in this example, granules smaller than 106 µm) was approximately 20%. The flowability of the mass was observed to be excellent.

Figure 2G:
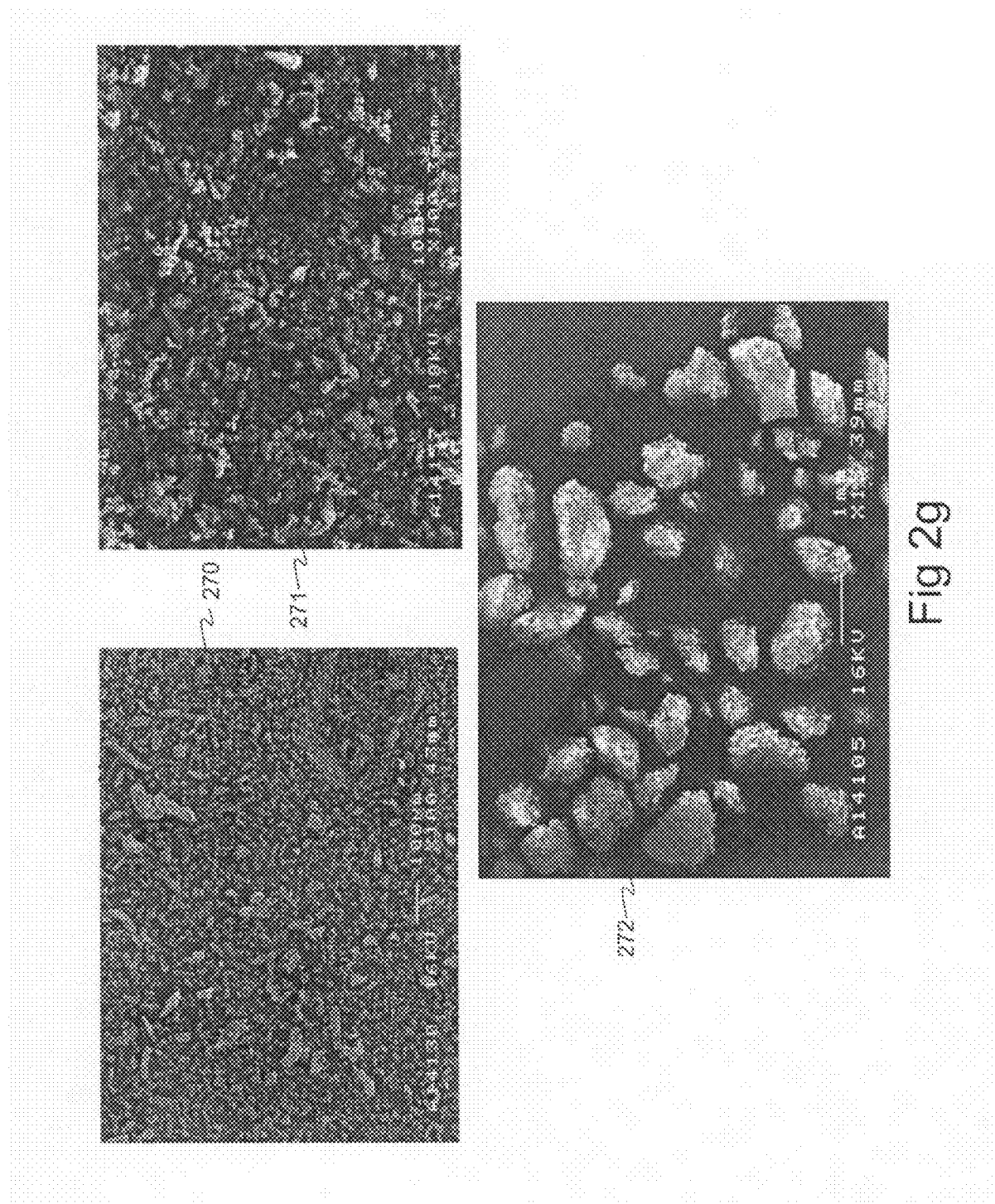
FIG. 2g illustrates an example about formation of granular mass of an embodiment of the present invention.

FIG. 2g illustrates formation of granules from raw material comprising 50% microcrystalline cellulose and 50% of maize starch. Image 270 shows a SEM-image of unprocessed raw material. Image 271 shows a SEM-image of compacted but not yet fractionated granular mass. Compaction force of 25 kN was used in the experiment. Image 272 shows a SEM-image of granular mass accepted by the fractionating device of an embodiment of the present invention. The magnification of images 270 and 271 is essentially similar and image 272 has 0.1× magnification in comparison to images 270 and 271. Image 270 shows practically no granules. In image 271, attention is drawn to the relatively small size of the granules produced in the compacting step. Granules in the compacted mass 271 created by the roller compactor and flake crusher (110 and 111 in FIGS. 1a and 1b) are generally smaller than 500 µm whereas majority of the granules 272 accepted by the fractionating device (see FIG. 4) are larger than 500 µm. This surprising observation makes inventors believe that new acceptable granules may be created and/or granules may further agglomerate during the fractionating phase of the method of an embodiment of the present invention.

Figure 2H:
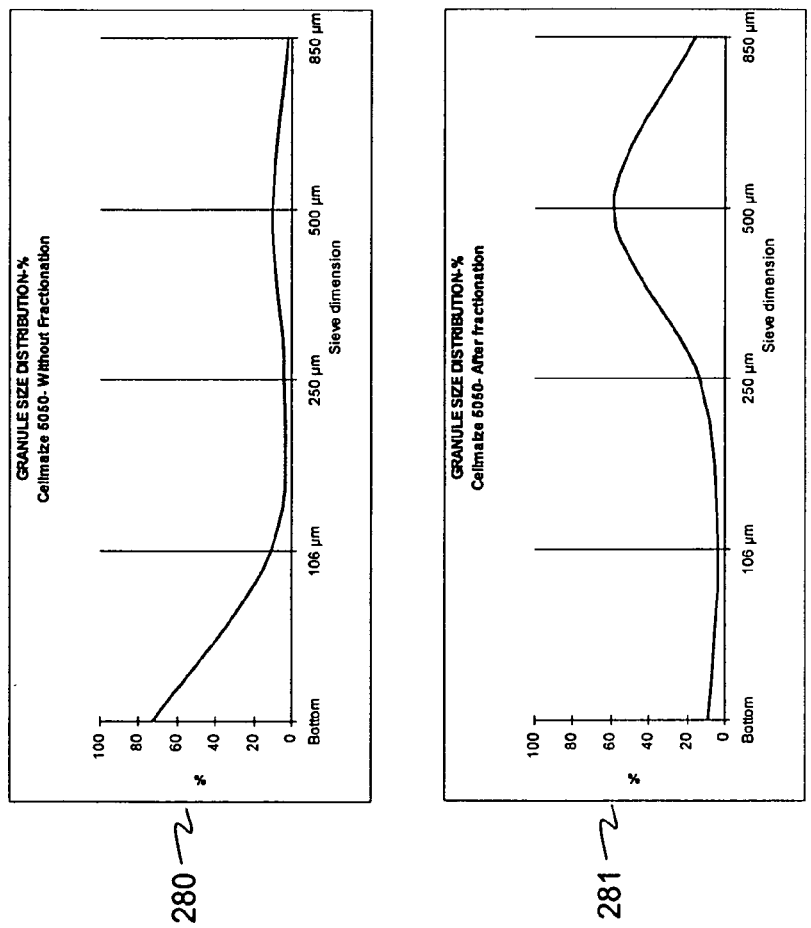
FIG. 2h shows particle size distribution diagrams of materials shown in FIG. 2g.

FIG. 2h shows particle size distribution charts of materials depicted in images 271 and 272 of FIG. 2g. According to the product certification data of raw materials used, the size distribution of particles of the raw material (not shown in figures) is such that practically all particles of the mass are smaller than 106 µm.

When the mass is compacted, the proportion of granules of acceptable size increases slightly as shown in image 280 but the majority (approximately 73%) of particles are still smaller than 106 µm. Image 281 shows that after fractionation, the proportion of granules larger than 106 µm increases significantly. The accepted fraction still contains about 10% of small granules and/or fine particles smaller than 106 µm. Despite the relatively large proportion of small granules and/or fine particles, the mass exhibits excellent flowability. The total proportion of granules accepted from the compacted mass in the fractionating step was approximately 10%. Thus, approximately 90% of the mass was rejected by the fractionating device.

FIG. 2i shows SEM-images of surfaces of granules manufactured using embodiments of the present invention. Different compaction forces have been used in the granulating process. The material shown comprises 50% of microcrystalline cellulose and 50% of maize starch. Images 290, 291, 292 depict granules produced using compaction force of 25 kN, 40 kN and 60 kN, respectively. Attention is drawn to the decreasing surface porosity when the compaction force is increased. Numerous pores are easily detectable in granules of images 290 and 291 whereas there are large dense areas in granule of image 292. Lack of pores on the surface of the granule may deteriorate at least some of the properties of the granular mass, e.g. flowability of the mass, tabletability of the mass and/or disintegration time of resulting tablet. Thus it is suggested that the optimal compaction force for producing granules from this raw material is probably below 60 kN. Although the SEM images 290, 291 don't show significant differences in the structure of the surface of the granule, the granular mass produced using compaction force of 25 kN form tablets with higher tensile strength and quicker disintegration time than the mass produced with compaction force of 40 kN.

Figure 3:
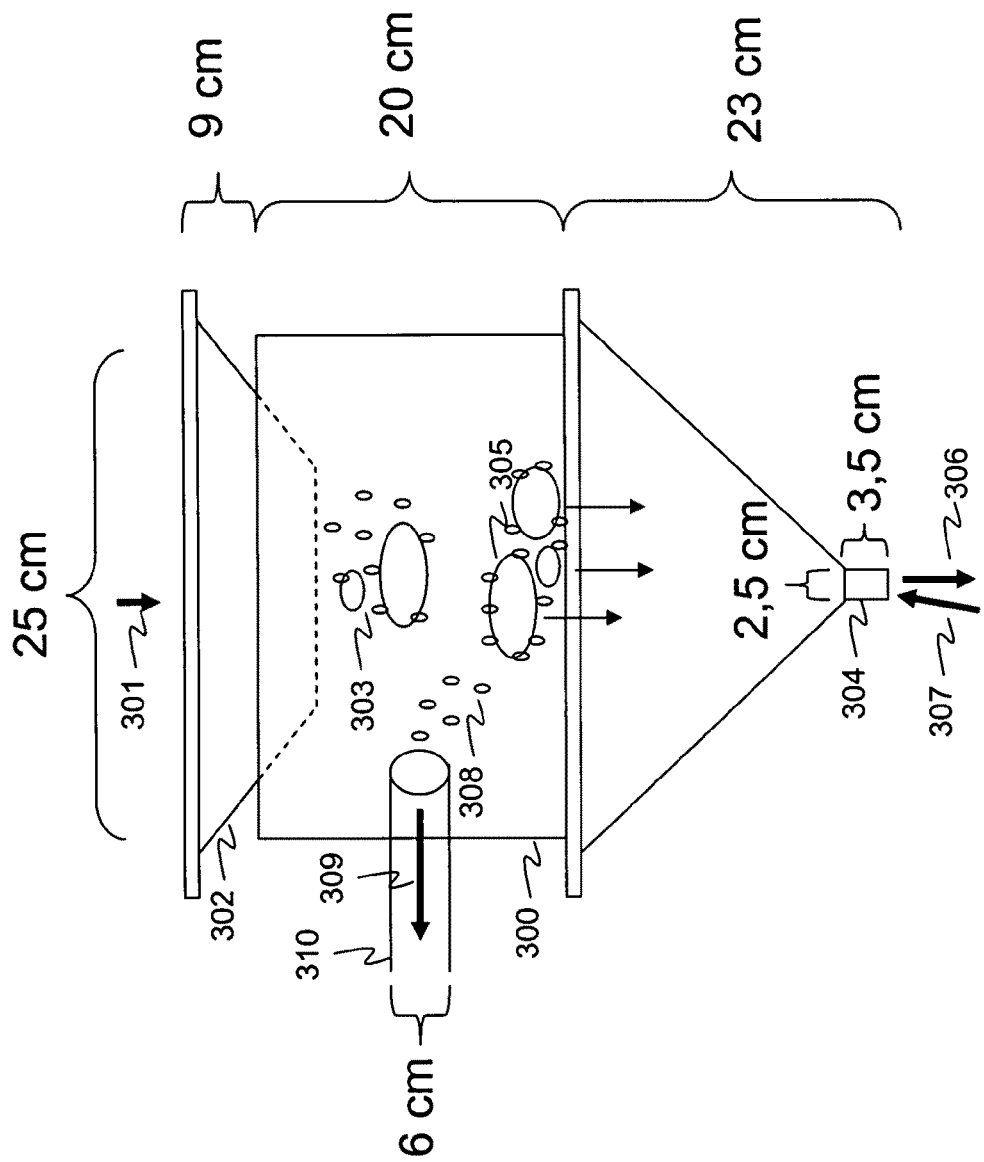
FIG. 3 shows an exemplary fractionating device according to an embodiment of the invention.

FIG. 3 shows an exemplary fractionating device for removing fine particles and/or small granules from the granulate mass 303 produced by the compactor. The device has a chamber 300 that contains apertures for different purposes. Input material 301 from the compactor and flake crusher is fed through one or multiple apertures 302. Gravity makes the material 305 flow downwards towards aperture 304 through which the accepted granulate mass 306 flows out of the system into a container. From the same aperture 304, carrier gas (air) 307 flows into the system. The gas may flow into the system also from some other aperture that is positioned such that the desired fine particle and/or small granules removing effect of the carrier gas flow is achieved. The carrier gas flows in a direction that is different from (countercurrent to) the flow of accepted granules. Accepted granules fall out of the fractionating device through tube 304 by effect of gravitation. While the granules are moving in the fractionating device 300, fine particles and/or small granules may agglomerate with other granules, thus making the granules grow further. The fine particles and/or small granules 308 are carried away from the fractionating device by the carrier gas flow 309 through aperture 310. There may be multiple apertures for the accepted granules as well as for the rejected fine particles and/or small granules.

Figure 4:
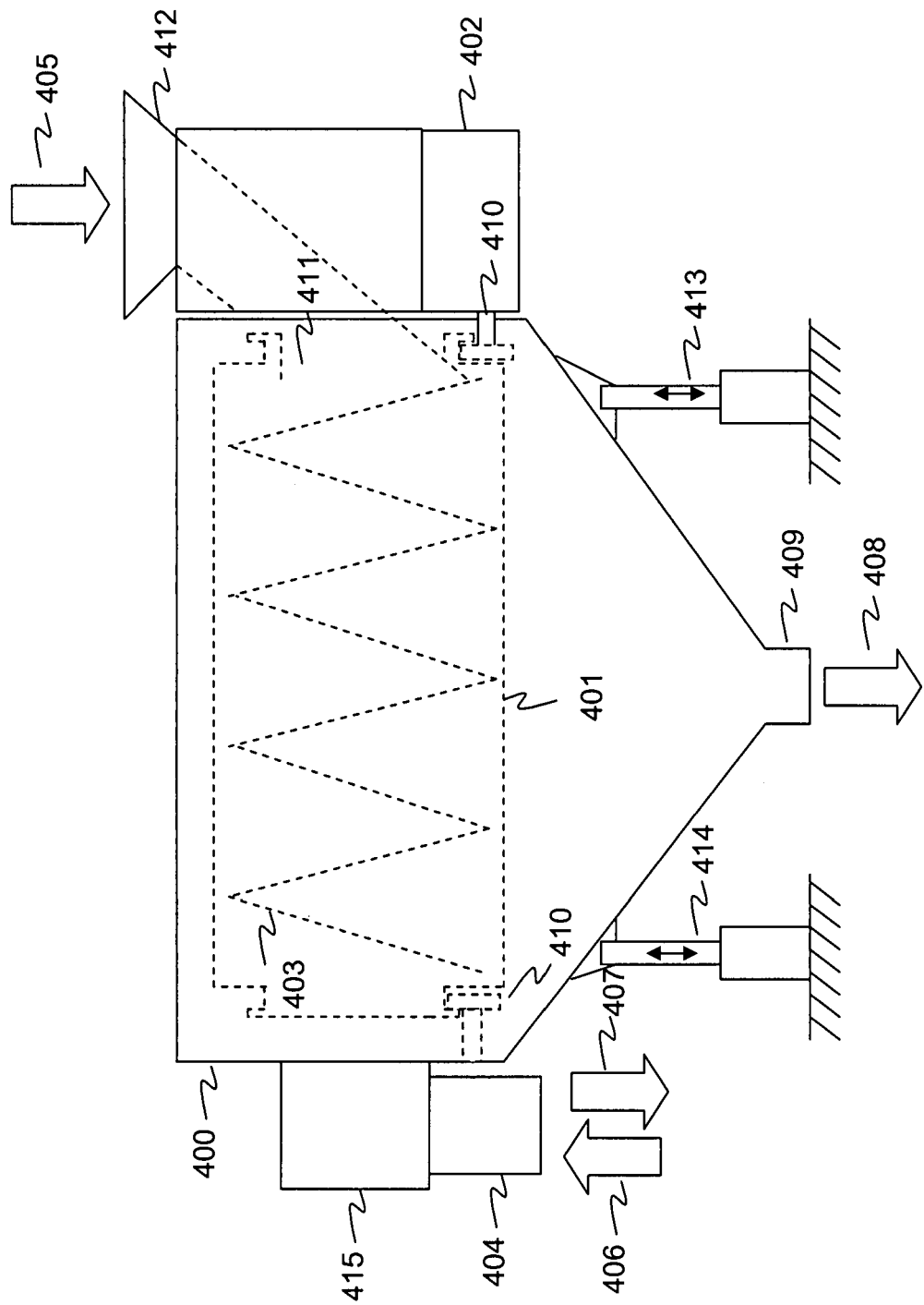
FIG. 4 shows an exemplary fractionating device that contains an additional rotating device usable according to an embodiment of the invention.

FIG. 4 illustrates an example of an enhanced fractionating device. In the figure, components and structures residing inside the device are drawn using dotted lines. The device 400 comprises a fractionating chamber and, mounted inside the chamber, an open ended cylinder (or cone-shaped device, not illustrated) 401 rotatably supported on rollers 410. The rotating speed of the cylinder can be adjusted to be for example the maximum available in the device of make ROTAB™ (Donsmark Process Technology A/S, Copenhagen, Denmark) and model 400EC/200. The jacket of the cylinder or cone may be perforated. There are no restrictions with regard to the number and shape of the possible apertures or their edges except for that the apertures should be constructed so that the gas (air) together with entrained fine particles is able to leave the cylinder through them. The apertures may be, for instance, round, oval or slots. In one embodiment, the apertures are round and they have been cut using laser cutting techniques. In one embodiment, the diameter of the round apertures is 1.5 mm. A drive motor 402 is arranged to rotate the cylinder at a suitable speed, e.g. at 100 RPM. A spiral structure 403 is provided inside the cylinder for transporting the solid material from the feed end 411 to the outlet 404 as the cylinder rotates. Instead of a spiral, various kinds of fins or other structures can be provided internally within the cylinder to obtain movement of the compacted material, and its interaction with the gas stream. The angle of inclination of the cylinder may be adjusted as required by, for instance, changing the position of the whole fractionating device 400 in its suspension structure 413, 414.

The powder 405 leaving the compacting device falls through a charge connection 412 into the feed end 411 of the cylinder and is transported by the spiral 403 towards an outlet tube 404. The carrier gas 406 flowing through the outlet 404 moves in the opposite direction to the accepted granules 407. Acceptable granules pass along in the cylinder 401, and fall through the outlet 404 to a product container (not shown) by effect of gravitation. Unacceptable fine particles and/or small granules that may be accompanying the acceptable granules to the tube 404 are generally conveyed back from the tube 404 to the cylinder 401 by the gas stream 406. In the present device, the outlet 404 is a downward pointing tube whose length is 70 mm and diameter is 40 mm. The rejected fraction of fine particles and/or small granules 408 together with the carrier gas stream flows to the feeding conveyor (see 102 in FIG. 1), through connection 409 for reprocessing. The granules may grow in size in the fractionating device 400 (or 300 in FIG. 3). This agglomeration may be caused e.g. by triboelectrification and electrostatic forces.

The properties of the accepted fraction may be influenced e.g. by changing the rotation speed of the cylinder, the angle of inclination of the cylinder, the pitch of the spiral, and the size, number and location and the shape of the apertures in the cylinder as well as by varying the flow rate of the carrier gas.

Figure 5B:
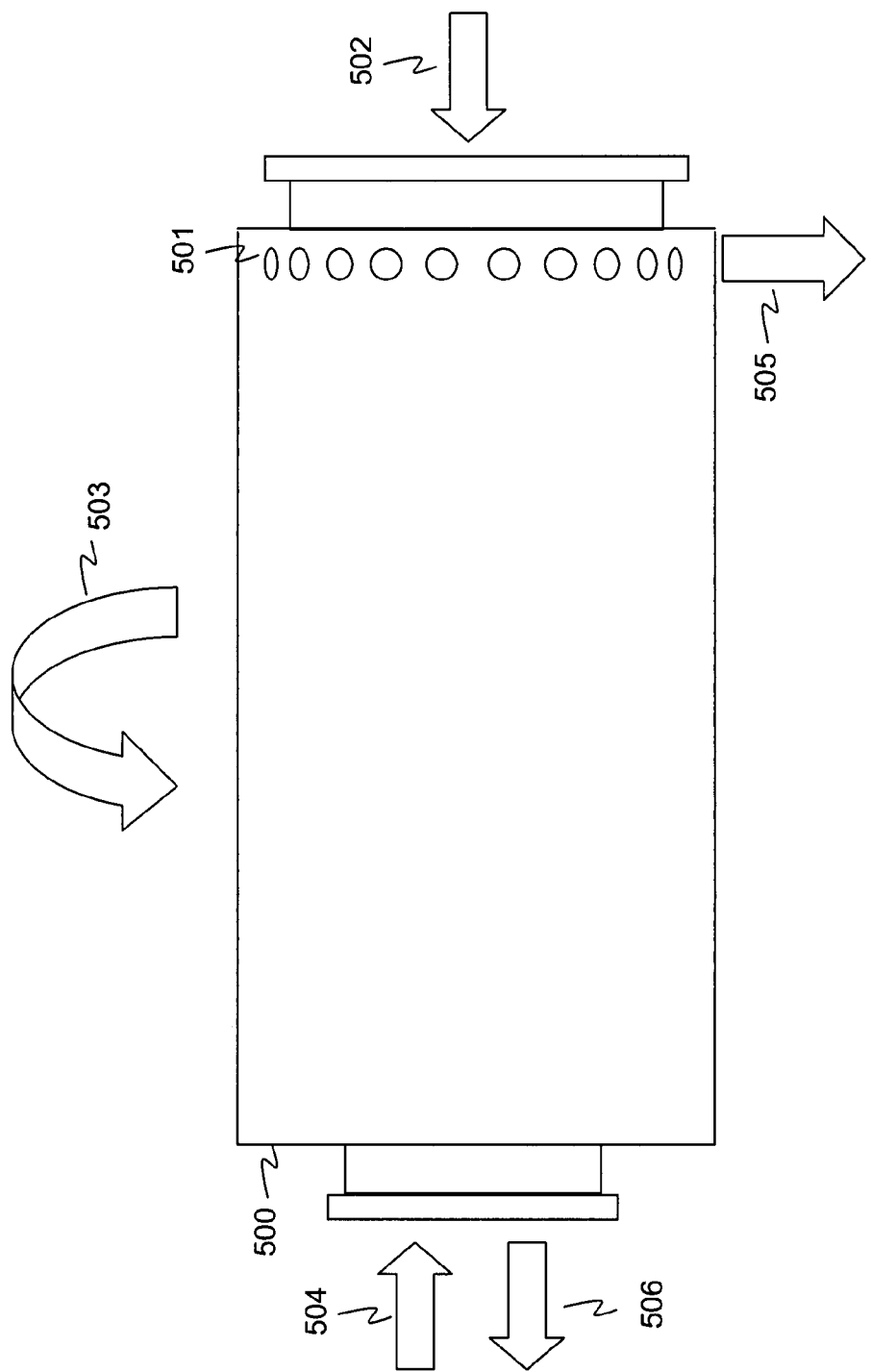

FIGS. 5*a* and 5*b* show two different forms of the cylinder-shaped device residing inside the fractionating device (see 400 in FIG. 4). A cylinder 500 has apertures 501 that in the FIG. 5*a* are situated throughout the jacket of the cylinder whereas in FIG. 5*b* there are apertures only in one end of the cylinder. The input material 502 that contains both granules and fine particles is fed to the rotating cylinder from one end of the cylinder. The rotating movement 503 of the cylinder 500 and the spiral (see 403 in FIG. 4) inside the cylinder push the input material towards the other end of the cylinder. While the material is moving in the cylinder, carrier gas flow 504 separates the acceptable granules from the rejected fine particles and/or small granules 505 which are conveyed out of the cylinder through apertures 501 with the carrier gas flow. The accepted granules 506 are eventually pushed out of the cylinder by the spiral structure that resides inside the cylinder.

Figure 5C:
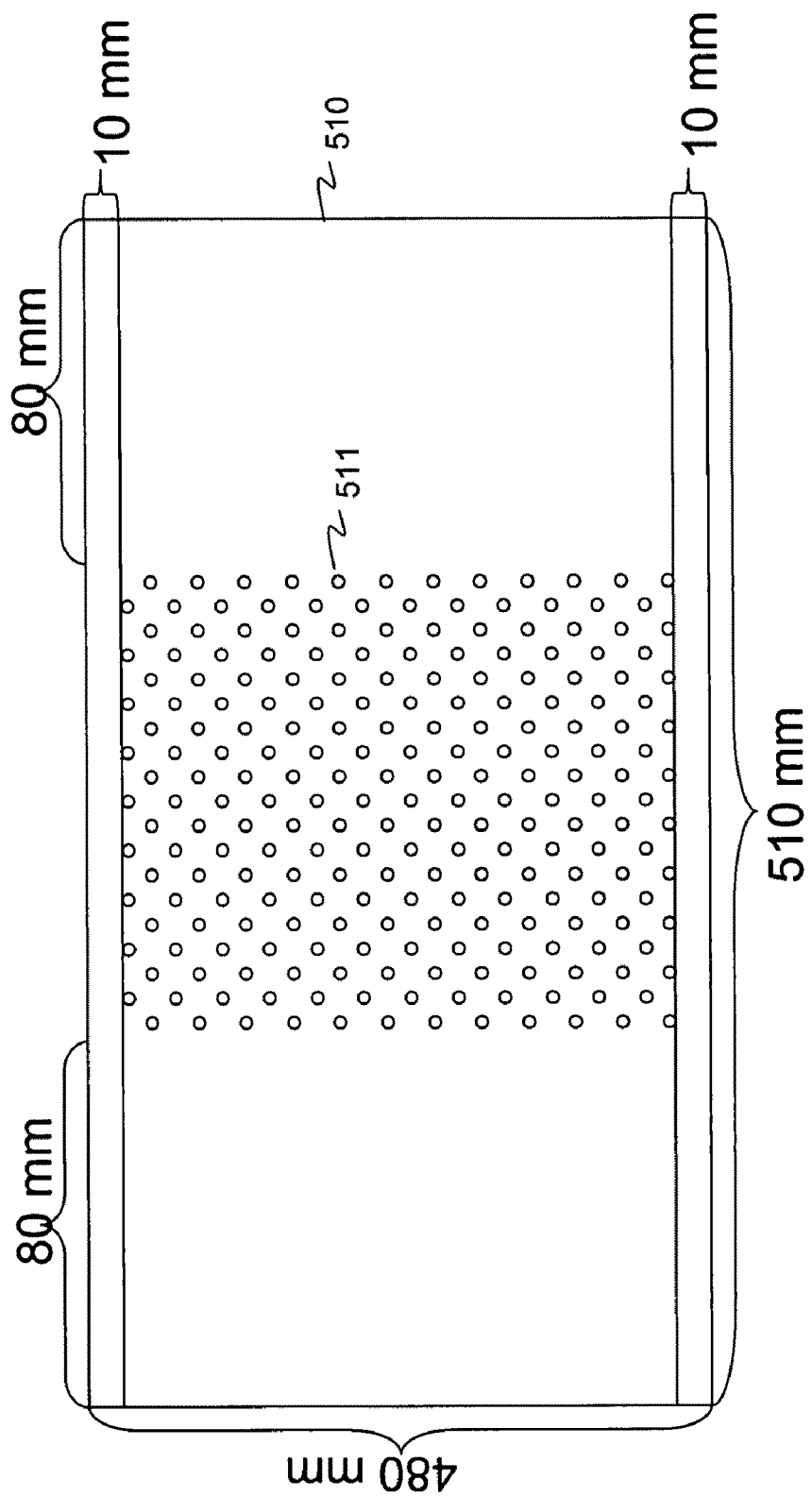
FIG. 5c shows an exemplary perforated steel sheet that may be used as part of a rotating device according to an embodiment of the present invention.

In the shown embodiment, the rotating device is a cylinder of diameter of 190 mm and length of 516 mm and comprises apertures each having a diameter of 1.5 mm and the apertures reside on average 6 mm from each other. The air stream that enters the fractionating device through aperture 404 (FIG. 4) is further led out of the fractioning chamber for reprocessing through an aperture (409 in FIG. 4) of 50 mm in diameter. Inside the cylinder there is a screw-shaped guiding structure that advances 80 mm per revolution towards the aperture of accepted material 506. The height of the guiding structure is 25 millimeters. FIG. 5*c* shows a drawing of an exemplary perforated stainless steel sheet that may be used to build a suitable cylinder. The thickness of the sheet is about 0.8 mm. The ROTAB™ device described above has been modified by changing the cylinder to one assembled from the steel sheet of FIG. 5*c* and the fractionating chamber has been changed to one having the shape similar to one shown in 400 of FIG. 4.

Although the devices shown in FIGS. 5*a* and 5*b* are open-ended and cylinder shaped, and the movement involved is a rotating movement, conveyor devices of other shapes and utilizing other kinds of movements may also be used to convey the mass in the fractionating air stream.

The device may optionally be adapted to improve its continuous processing capabilities. One such adaptation is disclosed in FIG. 6 where a dual filter assembly is illustrated. The majority of fine particles and/or small granules is separated from carrier gas, e.g. air, in cyclone 602 (see also 106 in FIG. 1*a* or 1*b*), but some fine particles and/or small granules may be sucked out of the cyclone with the carrier gas. Those particles may need to be filtered out before the carrier gas leaves the system. The filters 607*a*, 607*b* collect the fine particles and/or small granules until the filter is cleaned. One filter 607*a*, 607*b* may be active while the other is being cleaned e.g. by vibrating it. The valves 605, 612 may be used for guiding the gas flow through the active filter and for isolating the filter being cleaned from the gas stream. The powder resulting from the filter cleaning falls below the filter and further to a tube 609*a*, 609*b* when the valve 608*a*, 608*b* respectively is opened. In the other end of the tube, there may be a lower valve 610*a*, 610*b* that is opened after the upper valve 608*a*, 608*b* has been closed. Opening the lower valve causes the powder to fall back into the circulation for re-processing. This arrangement makes it possible to clean one of the filters while the apparatus is operational and the cleaning operation doesn't result in undesirable pressure shocks of carrier gas in the apparatus.

The apparatus may also optionally be equipped for example with sensors that measure the size of accepted granules in real-time. Such an arrangement is shown in FIG. 7. Accepted granules leave the fractionating device 700 through tube 701. Light emitting devices 702 as well as light sensitive sensors 703 have been installed in the tube to observe the size of the passing accepted granules. Based on the information created by the sensors, the control logic of the system may adjust the operating parameters of the apparatus. One such adjustable parameter may be for example the size of granules produced by the flake crushing screen 704. Another such adjustable parameter may be the gas flow rate of the system.

Figure 8:
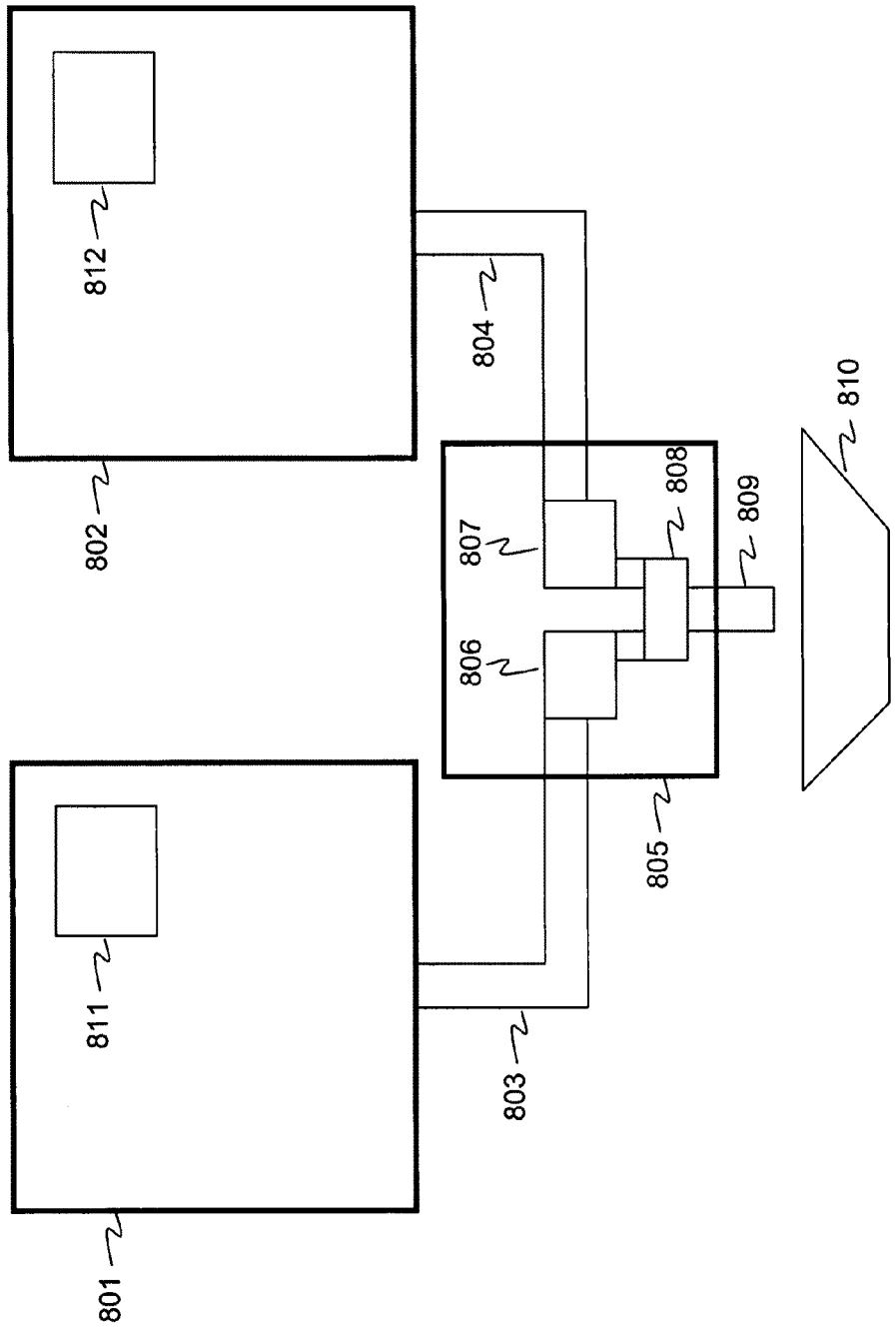
FIG. 8 shows an exemplary arrangement for mixing granulate masses from separately compacted substances.

FIG. 8 illustrates an exemplary optional arrangement for granulating powders separately and then mixing the granules together. The properties, e.g. disintegration time, of the end product, e.g. tablet, may be affected by granulating components of a formulation in multiple granulation processes vs. together in one process.

Granulation systems 801, 802 each produce granules from different substances (or from the same substance but with different granulation parameters such as compaction force or size of accepted granules). Each system has its own means 811, 812 of adjusting the granulation parameters. The accepted granules from each granulation system are led through a conveyor 803, 804 to a granule mixing device that has means 806, 807 to control the amount of each of the granules in the final mix. The mixing device may also have granule mixing means 808 to mix the granules together before the granulate mass flows to the container of final product 810 or directly to a tableting machine (not shown). The conveyor 803, 804 in FIG. 8 is a tube that leads to the mixing device, but the conveyor may also lead the granules into an intermediary storage container from which the mass may conveyed to the mixing device.

Figure 9:
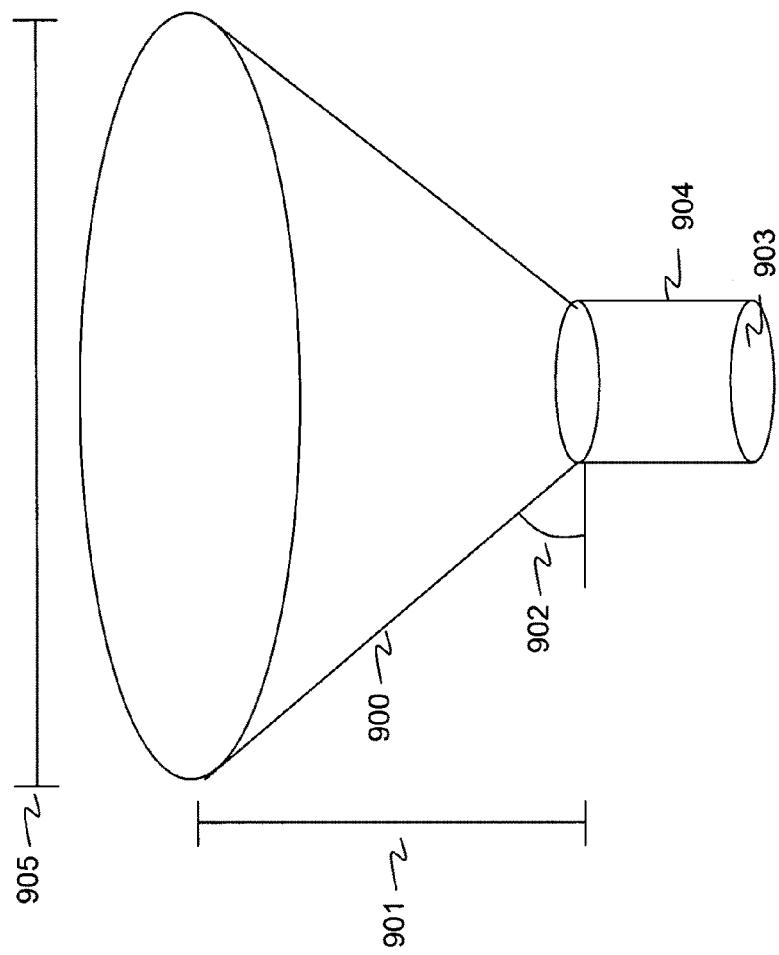
FIG. 9 shows an exemplary device for determining flowability of a powder or granulate mass.

FIG. 9 illustrates a simple device for measuring flowability of powder or granulate mass. Devices of different sizes are used for determining different degrees of flowability. The degree of flowability may be sufficient, good, very good or excellent.

The device for determining sufficient flowability has a smooth plastic surface cone 900 with a height 901 of 45 millimeters and with cone angle 902 of approximately 59 degrees and a round aperture 903 whose diameter is 12 millimeters. The length of tube 904 is 23 mm. In a flowability test procedure, the cone is filled with powder or granulate mass while the round aperture 903 is kept closed. The aperture is opened, cone is knocked lightly to start the flow and the flow of the powder through the aperture by mere gravitation force is observed. Additional shaking or other kind of movement of the cone during the test is not allowed. The material passes the flowability test if the cone substantially empties. "Substantial" here means that at least 85%, 90% or 95% of the powder leaves the cone.

The device for determining good flowability using the test procedure explained above has a smooth glass surface cone 900 with a height 901 of 50 millimeters and with cone diameter 905 of 70 mm and a round aperture 903 whose diameter is 7 millimeters. The length of tube 904 is 70 mm.

The device for determining very good flowability has a smooth plastic surface cone 900 with a height 901 of 35 millimeters and with cone diameter 905 of 48 mm and a round aperture 903 whose diameter is 4 millimeters. The length of tube 904 is 50 mm.

The device for determining excellent flowability has a smooth plastic surface cone 900 with a height 901 of 40 millimeters and with cone diameter 905 of 55 mm and a round aperture 903 whose diameter is 3 millimeters. The length of tube 904 is 60 mm.

Using the above mentioned or other embodiments of the present invention, it is possible to produce granules that have one or multiple of some desirable general characteristics, e.g. good flowability, good compressibility, good tabletability, quick disintegration time of a tablet and high drug load. We have observed that those characteristics are applicable to many APIs and excipients. Thus, some potentially time-consuming and expensive parts of the drug formulation design process of prior art may be avoided with many APIs. The embodiments shown are also relatively cost-efficient to build and use. For example, it is possible to build an arrangement that is capable of producing several kilograms or tens of kilograms of granules per hour. The process is also relatively simple and easy to control in comparison to e.g. wet granulation methods of prior art. In the shown embodiments, there are few parameters that may need to be adjusted.

Percentage (%) values given herein are by weight unless otherwise stated.

Mean values are geometric mean values unless otherwise stated.

The examples below describe characteristics of some typical granules and tablets achievable using the embodiments of the present invention.

EXAMPLES

To observe the characteristics of the granulate mass of various embodiments of the invention and their tabletability, a series of tests has been conducted. In all tests, method and apparatus described in this document (e.g. FIG. 1b and FIG. 4) has been used. The gas flow rate of the apparatus was adjusted so that the fractionating effect of the gas flow resulted in a granulate mass that had good, very good or excellent flowability. The gas flow rate in the tests was achieved operating the suction fan (BUSCH™ Mink MM 1202 AV) of the system at a default speed of approximately 1860 RPM. With some materials, the speed was altered from the default to achieve desired quality of the granulate mass.

The compaction force of the roller compactor was adjusted to produce granules with optimal tableting characteristics. The force used was recorded as kilonewtons as indicated by the roller compactor (HOSOKAWA Bepex Pharmapaktor L200/50P) used in the tests. The diameter of the rolls of the compactor is 200 mm and the working width of the rolls is 50 mm. The thickness of the ribbon produced by the compactor is about 4 mm. The rotating speed of the rolls is typically between 10 and 12 RPM. The exact rotating speed is adjusted by the roller compactor to achieve the desired compaction force. The default mesh size of the flake crushing screen is 1.00 mm. In some experiments, the mesh size of the flake crushing screen was altered from the default.

Unless specified differently, a rotating device as shown in FIG. 4 operating at about 100 RPM was used as the fractionating means of the apparatus of the tests. The default size of apertures in the cylinder of the rotating means was 1.5 mm.

In all tableting tests, 0.25% of magnesium stearate was added to the granulate mass prior to tableting as a lubricant.

Maize starch used in the tests was estimated to have particle size between 5 and 30 micrometers.

The tensile strength of the tablets has been measured using a measuring device of make MECMESIN™ (Mecmesin Limited, West Sussex, UK) and model BFG200N.

The particle size distribution of granulate mass was measured using stack of sieves. In the measurements, the stack of four sieves was shaken for 5 minutes using an Electromagnetic Sieve Shaker (manufacturer: C.I.S.A Cedaceria Industrial, S.L, model: RP 08) with power setting 6. The opening sizes of the sieves used were 850 μm, 500 μm, 250 μm and 106 μm.

Tableting Example 1

90% Acebutolol HCl

A powder mass of 5.0 kg having 90% of acebutolol HCl powder (mean particle size 27 micrometers) and 10% of starch was mixed. Compaction force of 40 kN was used to compact mass into granules having mean size of 877 micrometers and standard deviation of 1.421 after fractionation. The loose bulk density of the resulting mass was 0.68 g/ml and the mass had good flowability. Round tablets of 10 mm diameter and 500 mg of weight were created using tableting force of 6-8 kN. The average tensile strength of the tablet was 80N(N=10). Tablet disintegration time was observed to be about 6.5 minutes in water of approximately body temperature.

Tableting Example 2

20% Fluoxetine HCl

A powder mass having 20% (2.24 kg) of Fluoxetine HCl (Manufacturer: SIFAVITOR SpA, Casaletto Lodigiano. Italy. Batch no. 2700/01/06), 64% (7.168 kg) of microcrystalline cellulose (EMCOCEL CAS No. 9004-34-6, batch 5S3682) and 16%. (1.792 kg) of maize starch (CERESTAR Mat. no. 03401 batch 01015757) was mixed. Compaction force of 35 kN was used to compact mass into granules having mean size of 461 micrometers and standard deviation of 2.358 after fractionation. The mesh size of the flake crushing screen was set to 1.25 mm. The loose bulk density of the resulting mass was 0.595 g/ml and the mass had good flowability. Round tablets of 6 mm diameter and 112 mg of average weight (N=10, standard deviation=1.89%) were created using maximum tableting force that produced no capping. The average tensile strength of the tablet was 44 N(N=10, standard deviation=11.17%). Tablet disintegration time was observed to be about 10 seconds in water of approximately body temperature.

Tableting Example 3

60% Paracetamol

A powder mass of approximately 4.0 kg having 60% of paracetamol fine powder (Manufacturer: Mallinckrodt Inc.—Raleigh (USA)—Batch 7845906C563, 59% of particles smaller than 20 micrometers, 96% of particles smaller than 75 micrometers), 20% of microcrystalline cellulose (EMCOCEL CAS No. 9004-34-6, batch 5S3689, 50% of particles smaller than 71 micrometers) and 20% of maize starch (CERESTAR Mat. no. 03401, batch 01015757) was mixed. Compaction force of 30 kN was used to compact the mass into granules having mean size of 645 micrometers and standard deviation of 1.464 after fractionation. The mesh size of the flake crushing screen was set to 1.00 mm. The bulk density of the resulting mass was 0.586 g/ml and the mass had good flowability. Round convex tablets of 10 mm diameter and 454 mg of average weight (N=10, standard deviation=0.6%) were created using maximum tableting force that produced no capping. This was a very good result since hitherto it has been considered difficult, if not impossible, to produce high load tablets of paracetamol by compression of granulates prepared using dry granulation methods. The average tensile strength of the tablet was 49 N(N=10, standard deviation=12.73%). Tablet disintegration time was observed to be less than a minute in water of approximately body temperature.

Tableting Example 4

90% Sodium Valproate

A powder mass of 5.56 kg having 90% of Sodium valproate (Manufacturer: Chemische Fabrik Berg), 5% of hypromellose (PHARMACOAT 606, batch 5115055) and 5% of maize starch (CERESTAR Mat. no. 03401, batch 01015757) was mixed. Compaction force of 35 kN was used to compact mass into granules having mean size of 550 micrometers and standard deviation of 1.686. The mesh size of the flake crushing screen was set to 1.25 mm. The loose bulk density of the resulting mass was 0.532 g/ml and the mass had good flowability. Round convex tablets of 12 mm diameter and 560 mg of average weight (N=10, standard deviation=1.29%) were created using maximum tableting force that produced no capping. The average tensile strength of the tablet was 84 N(N=10, standard deviation=11.80%). Because of the slow-release characteristics introduced by hypromellose as excipient, tablet disintegration time was observed to be 40 minutes in water of approximately body temperature.

Tableting Example 5

50% Ketoprofen

A powder mass of approximately 8.0 kg having 50% of ketoprofen (Manufacturer: Ketoprofen S.I.M.S. Societa italiana medicinali Scandicci, batch 121.087, 79% or particles smaller than 60 micrometers) and 50% of maize starch (CERESTAR Mat. no. 03401, batch SB4944) was mixed. Compaction force of 40 kN was used to compact the mass into granules having mean size of 900 micrometers and standard deviation of 1.418. The mesh size of the flake crushing screen was set to 1.00 mm. The loose bulk density of the resulting mass was 0.625 g/ml and the mass had good flowability. Round convex tablets of 6 mm diameter and 94 mg of average weight (N=10, standard deviation=1.94%) were created using maximum tableting force that produced no capping. The average tensile strength of the tablet was 39 N(N=10, standard deviation=14.56%). Tablet disintegration time was observed to be about 10 seconds in water of approximately body temperature.

Tableting Example 6

80% Metformin HCl

Approximately 4.0 kg of powder mass having 100% of metformin HCl (Supplier: SIMS trading (Firenze, Italy), batch 21.039) was compacted using compaction force of 35 kN to produce granules having mean size of 668 micrometers and standard deviation of 1.554. The mesh size of the flake crushing screen was set to 1.00 mm. The loose bulk density of the resulting mass was 0.694 g/ml and the mass had good flowability. Separately, excipient granules containing 70% of microcrystalline cellulose (EMCOCEL CAS No. 9004-34-6, batch 5S3689) and 30% of maize starch (CERESTAR Mat. no. 03401, batch 01015757) was mixed and granulated using the same compaction force. Then 80% of metformin granules were mixed with 20% of excipient granules and compressed into tablets. Round convex tablets of 12 mm diameter and containing 500 mg of metformin were created using maximum tableting force that produced no capping. The average tensile strength of the tablet was 59 N(N=3). Tablet disintegration time was not measured.

In addition to tableting examples, compressibility and flowability of granulate mass of embodiments of the invention was tested by measuring the Hausner ratio of the mass and observing the flowability of the mass. Methods usable for calculating Hausner ratio and observing flowability of the mass have been described earlier in this disclosure.

Flowability Example 1

100% Paracetamol

A powder mass of 4.0 kg having 100% paracetamol (Manufacturer: Mallinckrodt Inc.—Raleigh (USA)—Batch 6088906C107) was compacted using compaction force of 12 kN and flake crushing screen mesh size of 1.00 mm into granules having mean size of 708 micrometers and standard deviation of 1.349 after fractionation. 0.58% of the granules of the mass had diameter of smaller than 106 micrometers. The bulk density of the resulting mass was 0.610 g/ml and tapped bulk density was 0.758 g/ml. The Hausner ratio of the mass was calculated to be 1.24. Despite the relatively high compressibility as indicated by the Hausner ratio, the flowability of the mass was observed to be excellent.

Flowability Example 2

90% Metformin HCl

A powder mass having 90% (4.0 kg) of Metformin (METFORMIN HYDROCHLORIDE USP, BATCH N. 17003742, USV LIMITED, B.S.D. Marg. Govandi, Mumbay 400 088, INDIA), 8% (356 g) of microcrystalline cellulose (EMCOCEL CAS No. 9004-34-6 Batch 5S3682) and 2% (88g) of maize starch (CERESTAR Mat. no. 03401, batch 01015757) was mixed. Compaction force of 30 kN, flake crushing screen mesh size of 1.00 mm and suction fan speed of 2100 RPM was used to produce granules having mean size of 477 micrometers and standard deviation of 2.030 after fractionation. 11.0% of the granules of the mass had diameter of smaller than 106 micrometers. The loose bulk density of the resulting mass was 0.581 g/ml and tapped bulk density was 0.714 g/ml. The Hausner ratio of the mass was measured to be 1.23. Despite the relatively high compressibility as indicated by the Hausner ratio, the flowability of the mass was observed to be excellent. When experimenting with metformin, the inventors have also made a surprising observation that although 100% metformin fine powder exhibits heavy agglomeration (forming large, hard agglomerates) when stored in room temperature and ambient humidity, 100% metformin granules made of such powder using a method of the invention show practically no such agglomeration during storage time.

Flowability Example 3

Excipient

A powder mass of approximately 3.0 kg containing 70% of microcrystalline cellulose (EMCOCEL CAS No. 9004-34-6 Batch 5S3689) and 30% of maize starch (CERESTAR Mat. no. 03401, batch 01015757) was mixed. Compaction force of 16 kN and flake crushing screen mesh size of 1.00 mm was used to produce granules having mean size of 318 micrometers and standard deviation of 2.159 after fractionation. 19.6% of the granules of the mass had diameter of smaller than 106 micrometers. The loose bulk density of the resulting mass was 0.379 g/ml and tapped bulk density was 0.510 g/ml. The Hausner ratio of the mass was measured to be 1.35. Despite the high compressibility of the mass as indicated by the Hausner ratio, the flowability was observed to be excellent.

Flowability Example 4

20% Ketoprofen

A powder mass of approximately 4.0 kg containing 20% of ketoprofen (S.I.M.S. Societa italiana medicinali Scandicci, batch 121.087) and 80% of microcrystalline cellulose (EMCOCEL CAS No. 9004-34-6 Batch 5S3689) was mixed. Compaction force of 24 kN and flake crushing screen mesh size of 0.71 mm was used to produce granules. When the suction fan speed of the system was set at 1980 RPM, the mean size of the accepted granules was 304 micrometers and standard deviation was 2.275 after fractionation. 23.0% of the mass had particle size smaller than 106 micrometers. The loose bulk density of the mass was 0.510 g/ml and tapped bulk density was 0.676 g/ml. The Hausner ratio of the mass was measured to be 1.325. The flowability of the mass was observed to be sufficient. When the suction fan speed of the system was set at 2400 RPM, the mean size of the accepted granules was 357 micrometers and standard deviation was 2.121 after fractionation. 13.7% of the mass had particle size smaller than 106 micrometers. The loose bulk density of the mass was 0.521 g/ml and tapped bulk density was 0.714 g/ml. The Hausner ratio of the mass was measured to be 1.371. The flowability of the mass was observed to be excellent. This example shows that by varying the gas flow rate of the system, granulate mass with different flow characteristics may be obtained. This example also indicates that, contrary to what is taught in prior art, e.g. U.S. Pat. No. 6,752,939, the Hausner ratio doesn't necessarily predict the flowability of the granulate mass. For example, the granule size distribution of the granular mass may have greater effect on flowability than the compressibility of the granulate mass. Good compressibility and flowability may thus co-exist in the same granulate mass.

Capacity Example

The embodiments described in this disclosure are capable of producing significant amounts of granulate mass. In a capacity test of one embodiment comprising the fractionating device of FIG. 4, 5.98 kg of Paracetamol (7845 Paracetamol Fine Powder—Mallinckrodt Inc.—Raleigh (USA)—Batch 7845906C563), 10.69 kg of Microcrystalline Cellulose (CAS no. 9004-34-6—JRS PHARMA LP—Patterson (USA)—Batch 5S3689), 37.10 kg of maize starch (CERESTAR Mat. n. 03401 Batch 01015757), 12.19 kg of lactose (LACTOSE MONOHYDRATE—DMV International Pharmatose 80M DP5500 Batch 10209285 906535704), 34.04 kg of cellulose ("Technocel"—CFF GmbH—Gehren Germany—Batch G13060620) were mixed and granulated using compaction force of ca. 40 kN and suction fan speed of 2160 RPM. The apparatus was running for two hours and 38 minutes producing 94.66 kg of granules which had at least good flowability characteristics.

Fractionating Example 1

A powder mass of approximately 5.0 kg containing 50% of microcrystalline cellulose (EMCOCEL CAS No. 9004-34-6 Batch 5S3689) and 50% of maize starch (CERESTAR Mat. no. 03401, batch 01015757) was mixed and granulated. Reprocessing of the rejected fraction was prevented in the granulation process. To achieve this, the mass to be processed was manually fed to the intermediate vessel (107 in FIG. 1*b*) from where it was conveyed to the compactor (110 in FIG. 1*b*) by opening the valve (109 in FIG. 1*b*) before starting the process. The process was then started and the mass of 5.0 kg was granulated and fractionated. During the processing, the valve (109 in FIG. 1*b*) was kept shut to prevent re-processing of the rejected fraction. Compaction force of 40 kN and flake crushing screen mesh size of 1.00 mm was used to produce granules having mean size of 523 micrometers (standard deviation 1.70) after fractionation. The test run produced 1630 g (32.6%) of accepted granules. A SEM image of the surface of an accepted granule is shown in image 291 of FIG. 2*i*. The rest of the mass was rejected by the fractionating device. 4.0% of the granules/particles of the accepted mass had diameter of smaller than 106 micrometers. The loose bulk density of the resulting mass was 0.56 g/ml and tapped bulk density was 0.641 g/ml. The Hausner ratio of the mass was measured to be 1.15. The flowability of the accepted fraction was observed to be excellent. On the other hand, the flowability of the rejected fraction was observed to be insufficient.

The rejected fraction contained 16.4% of granules larger than 250 micrometers whereas the accepted fraction contained 92% of granules larger than 250 micrometers.

To observe the tabletability of the accepted fraction of the granulate mass, 0.5% of magnesium stearate was added to the mass and tablets of average weight of 588 mg were produced. The average tensile strength of the tablet (N=6) was measured to be 23,56N and standard deviation was 1,308. The disintegration time of the tablet was observed to be about 12 seconds.

Fractionating Example 2

A powder mass of approximately 4.0 kg containing 50% of microcrystalline cellulose (EMCOCEL CAS No. 9004-34-6

Batch 5S3689) and 50% of maize starch (CERESTAR Mat. no. 03401, batch 01015757) was mixed and granulated. Unlike in the above examples, a fractionating device according to the embodiments of FIGS. 1a and 3 of this disclosure was used in the fractionating step of the process. Reprocessing of the rejected fraction was prevented in the granulation process. To achieve this, the mass to be processed was manually fed to the intermediate vessel (107 in FIG. 1a) from where it was conveyed to the compactor (110 in FIG. 1a) by opening the valve (109 in FIG. 1a) before starting the process. The process was then started and the mass of 4 kg was granulated and fractionated. During the processing, the valve (109 in FIG. 1a) was kept shut to prevent re-processing of the rejected fraction. Compaction force of 16 kN and flake crushing screen mesh size of 1.00 mm was used to produce granules having mean size of 437 micrometers (standard deviation 2.42) after fractionation. The test run produced 670 g (16.75%) of accepted granules. The rest of the mass was rejected by the fractionating device. 20.9% of the granules/particles of the accepted mass had diameter of smaller than 106 micrometers. The loose bulk density of the resulting mass was 0.455 g/ml and tapped bulk density was 0.568 g/ml. The Hausner ratio of the mass was measured to be 1.248. Despite the high compressibility of the accepted mass as indicated by the Hausner ratio, the flowability was observed to be excellent. On the other hand, the flowability of the rejected fraction was observed to be insufficient.

The rejected fraction contained 7.1% of granules larger than 250 micrometers whereas the accepted fraction contained 68.4% of granules larger than 250 micrometers.

To observe the tabletability of the accepted fraction of the granulate mass, 0.5% of magnesium stearate was added to the mass and tablets of average weight of 584 mg were produced. The average tensile strength of the tablet was measured to be 63,34N and standard deviation was 6,78 (N=6). It is noteworthy that the tensile strength of the tablet is significantly higher than in fractionating example 1. The disintegration time of the tablet was observed to be about 12 seconds.

To a person skilled in the art, the foregoing exemplary embodiments illustrate the model presented in this application whereby it is possible to design different methods, systems, granules and tablets, which in obvious ways utilize the inventive idea presented in this application.

The foregoing references set forth in the specification are hereby incorporated by reference.

The invention claimed is:

1. A method for producing granules from a powder, comprising applying a low compaction force to the powder to produce a compacted mass comprising a mixture of fine particles and granules and separating fine particles from the granules by entraining fine particles in a gas stream in which the compacted mass flows, wherein the direction of the flow of gas stream has a component which is contrary to that of flow of the compacted mass, and wherein the fine particles are separated from the granules by means of an apparatus comprising fractionating means wherein the fractionating means comprises a rotating device along the axis of which the compacted mass is moved in said gas stream.

2. A method according to claim 1 wherein the compaction force is sufficiently low that 75% or less by weight of the powder is compacted into acceptable granules having particle size larger than 150 μm and the rest remains as fine particles and/or small granules.

3. A method according to claim 1 wherein the compaction force is the compaction force of 60 kN or less in a roller compactor.

4. A method according to claim 3 wherein the compaction force is 45 kN or less in a roller compactor.

5. A method according to claim 1 wherein the compaction force is 16 kN or more.

6. A method according to 1 wherein the compaction force is applied to the powder by a process comprising use of a roller compactor to generate a ribbon of compacted powder which is broken up to produce granules.

7. A method according to claim 1 wherein the direction of flow of the gas stream is substantially contrary to that of the direction of flow of the compacted mass.

8. A method according to claim 1, wherein said compacted mass is moved in said as stream by mechanical means.

9. A method according to claim 1 wherein the rotating device is a cylinder or cone.

10. A method according to claim 1 wherein movement of the compacted mass along the axis of the rotating device is guided by means of a spiral structure.

11. A method according to claim 1 wherein the fractionating means contains apertures through which the fine particles and/or small grannies are entrained.

12. A method according to claim 11 for producing granules of mean desired size x wherein the apertures have a minimum dimension of 1.0×.

13. A method according to claim 11 wherein the apertures have a minimum dimension of 250 μm.

14. A method according to claim 1 wherein the fractionating means does not require passage of the compacted mass through any sieve.

15. A method according to claim 1 wherein the residence time of the compacted mass within the fractionating means is at least 2 seconds.

16. A method according to claim 1, characterized in that said powder comprises an excipient usable in pharmaceutical products and/or an active pharmaceutical ingredient.

17. A method according to claim 16 wherein the powder comprises an active pharmaceutical ingredient selected from at least one of acebutolol fluoxetine paracetamol, sodium valproate, ketoprofen and metformin MCI.

18. A method according to claim 16 wherein said powder contains an amount of active pharmaceutical ingredient of at least 60%.

19. A method according to claim 18 wherein said powder contains an amount of active pharmaceutical ingredient of at least 80%.

20. A method according to claim 1 wherein the entrained fine particles and/or small granules are re-circulated for compaction.

21. A method according to claim 1 wherein the powder is conveyed from a reservoir to the means to apply the compaction force by means comprising use of a pneumatic conveyor.

22. A method according to claim 1 further comprising the step of the collecting granules.

23. A method according to claim 22 which is run as a continuous process.

24. A dry-granulated granulate mass containing granules obtainable according to the method of claim 22.

* * * * *